US009326994B2

(12) United States Patent
Dhal et al.

(10) Patent No.: US 9,326,994 B2
(45) Date of Patent: May 3, 2016

(54) AMINE FUNCTIONAL POLYAMIDES

(71) Applicant: GENZYME CORPORATION, Cambridge, MA (US)

(72) Inventors: Pradeep Dhal, Westford, MA (US); Kanwen Yang, Brighton, MA (US); Robert J. Miller, E. Bridgewater, MA (US); S Randall Holmes-Farley, Arlington, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 14/210,571

(22) Filed: Mar. 14, 2014

(65) Prior Publication Data

US 2014/0275469 A1    Sep. 18, 2014

Related U.S. Application Data

(60) Provisional application No. 61/790,231, filed on Mar. 15, 2013.

(51) Int. Cl.
| | |
|---|---|
| *C08G 69/26* | (2006.01) |
| *A61K 31/787* | (2006.01) |
| *A61K 47/48* | (2006.01) |
| *C08G 63/672* | (2006.01) |
| *C08G 73/02* | (2006.01) |
| *C08G 73/06* | (2006.01) |

(52) U.S. Cl.
CPC ......... *A61K 31/787* (2013.01); *A61K 47/48023* (2013.01); *A61K 47/48215* (2013.01); *C08G 63/672* (2013.01); *C08G 69/26* (2013.01); *C08G 73/028* (2013.01); *C08G 73/0273* (2013.01); *C08G 73/0627* (2013.01)

(58) Field of Classification Search
CPC ..... A61K 31/787; C08G 63/672; C08G 69/26
See application file for complete search history.

(56) References Cited

U.S. PATENT DOCUMENTS

2012/0070383 A1* 3/2012 Almutairi et al. .... A61K 49/126
424/9.36
2012/0295922 A1 11/2012 Scott et al.

FOREIGN PATENT DOCUMENTS

| WO | WO 01/93878 | 12/2001 |
| WO | WO 2010/054269 | 5/2010 |
| WO | WO 2012/151554 | 8/2012 |

OTHER PUBLICATIONS

Tumiatti et al (Structure-Activity Relationships of Acetylcholinesterase Noncovalent Inhibitors Based on a Polyamine Backbone. 3. Effect of Replacing the Inner Polymethylene Chain with Cyclic Moieties, J. Med. Chem. 2004, 47, 6490-6498), Dec. 2004.*
USPTO strucure search, Jul. 2015.*
Zhang, et al., Erosion of Multilayered Films Fabricated from Degradable Polyamines: Characterization and Evidence in Support of a Mechanism That Involves Polymer Hydrolysis, Journal of Polymer Science: Part A: Polymer Chemistry, vol. 44, pp, 5161-5173, (2006).
Malgesini, et al., Poly(Amido-Amine)s Carrying Primary Amino Groups as Side Substituents, Macromol. Biosci., (2003), vol. 3, pp. 59-66.
Werthen, et al., Pseudomonas Aeruginosa-induced Infection and Degradation of Human Wound Fluid and Skin Proteins Ex Vivo are Eradicated by a Synthetic Cationic Polymer, Journal of Antimicrobiol Chemotherapy, (2004), vol. 54, pp. 772-779.
Mowery, et al., Structure-Activity Relationships Among Random Nylon-3 Copolymers That Mimic Antibacterial Horst-Defense Peptides, J. Am, Chem. Soc., (2000), vol. 131, no. 28, pp. 9735-9745.
Zasloff, Antimicrobial Peptides of Multicellular Organisms, Nature, vol. 415, (2002), pp,.389-395.
Lienkamp, et al., Antibacterial Peptidomimetics: Polymeric Synthetic Mimics of Antimicrobial Peptides, Adv Polym Sci, (2010), pp. 1-32.
Thaker, et al., Synthetic Mimics et Antimicrobial Peptides from Triaryl Scaffolds, Journal of Medicinal Chemistry. (2011), vol. 54, pp. 2241-2254
Tashro, Antibacterial and Bacterium Adsorbing Macromolecules, Macromol. Mater. Eng., (2001), vol. 286, No. 2, pp. 63-87.
Ou, et al., Novel Biodegradable Poly(Disulfide Amine)s for Gene Delivery With High Efficiency and Low Cytotoxicity, Bioconjugate Chem., (2008), vol, 19, pp. 626-633.
Ferruta, et al., Poly(Amido-Amines): Biomedical Applications, Macromol. Rapid Commun., (2002), vol. 23, pp. 332-355.
Watson, et al., Amphipathic 13-Strand Mimic as Potential Membrane Disruptive Antibiotics, J. Org. Chem., (2009), vol. 74, pp. 5953-5960.
Lienkamp, et al., "Doubly Selective" Antimicrobial Polymer: How Do They Differentiate between Bacteria?, Chem. Eur. J., (2009), vol. 15, pp. 11710-11715.
Rawlinson, et al., Antibacterial Effects of Poly(2-(Dimethylamino Etyl)Methacrylate) Against Selected Gram-Positive and Gram-Negative Bacteria, Biomacromolecules, (2010), vol. 11, pp. 443-453.
Kuroda, et al., The Role of Hydrophobicity in the Antimicrobial and Hemolytic Activities of Polymethacrylate Derivatives, Chem. Eur. J., (2009), vol. 15, pp. 1123-1133.
Jacobs, et al. Validation of the Children's international Mucositis Evaluation Scale (ChIMES) in Paediatric Cancer and SCT, British Journal of Cancer. (2013), vol. 109, pp. 2512-2522.
Mateos-Timoneda, et al., Poly(Amide Amine)s as Gene Delivery Vectors: Effect of Quaternary Nicotinamide Moieties in the Side Chains, ChemMedChem, (2008), vol. 3, pp. 478-486.

(Continued)

*Primary Examiner* — Gregory Listvoyb
(74) *Attorney, Agent, or Firm* — Chandra Adams

(57) ABSTRACT

Amine functional polyamides comprise amine and ammonium groups along the polymer chain. Amine functional polyamides can be used as pharmaceutical agents and in pharmaceutical compositions. The amine functional polyamides are particularly useful in the treatment or prevention of mucositis and infection, specifically oral mucositis, surgical site infection, and lung infection associated with cystic fibrosis.

22 Claims, 1 Drawing Sheet

(56) References Cited

OTHER PUBLICATIONS

Ranucci, et al., Poly(Amidoamine)s With 2-Dithiopyridine Side Substituents as Intermediates to Peptide-Polymer Conjugates, Macromol. Rapid Communications, (2007) vol. 28, pp. 1243-1250.

Beyth, et al., Polyethyleneimine Nanoparticles Incorporated into Resin Composite Cause Cell Death and Trigger Biofilm Stress In Vivo, PNAS, (2010), vol. 107, No. 51, pp. 22038-22043.

Ou, et al., A Family of Bioreducible Poly (Disulfide Amine)s for Gene Delivery, Biomaterials, vol. 30, (2009), pp. 5804-4814.

Chongsiriwatana, et al., Short Alkylated Peptoid Mimics of Antimicrobial Lipopeptides, Antimicrobial Agents and Chemotherapy. (2011), pp. 417-420.

International Search Report for WO2014/150338 dated Sep. 25, 2014.

Mangram, et al., Guideline for the Prevention of Surgical Site Infection. Infection Control and Hospital Epidemiology, vol. 20, No. 4. pp. 247-278, (1999).

Yu, et al., Ivacaftor Potentiation of Multiple CFTR Channels With Gating Mutations. Journal of Cystic Fibrosis, vol. 11, (2012), pp. 237-245.

Tummler, et al., Cystic Fibrosis: An Inherited Susceptibility to Bacterial Respiratory Infections, Molecular Medicine Today, (1999), vol. 5, pp. 351-358.

Moreau-Marquis, et al., Tobramycin and FDA-Approved Iron Chelators Eliminate Pseudomonas Aeruginosa Biofilms on Cystic Fibrosis Cell, American Journal of Respiratory Cell and Molecular Biology, vol. 41, (2009), pp. 305-313.

Hoiby, et al., Eradication of Early Pseudomonas Aeruginosa Infection, Journal of Cystic Fibrosis, vol. 4, (2005), 49-54.

Nichols, Preventing Surgical Site Infections: A Surgeon's Perspective, Emerging Infectious Disease Journal. vol. 7, No. 2, (2001), pp. 1-15.

\* cited by examiner

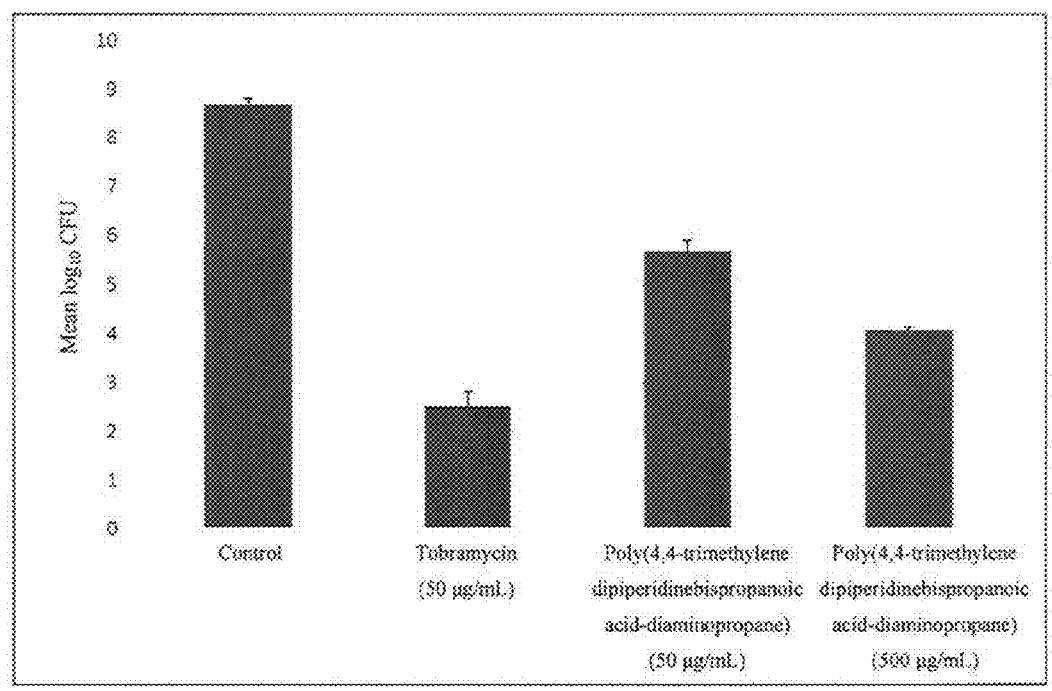

AMINE FUNCTIONAL POLYAMIDES

STATEMENT REGARDING FEDERALLY SPONSORED RESEARCH

Not applicable

THE NAMES OF THE PARTIES TO A JOINT RESEARCH AGREEMENT

Not applicable

INCORPORATION-BY-REFERENCE OF MATERIAL SUBMITTED ON COMPACT DISC

Not applicable

BACKGROUND OF THE INVENTION

1. Field of the Invention

This invention relates to amine functional polyamides. Amine functional polyamides comprise amine and ammonium groups along the polymer chain. This invention further relates to the use of amine functional polyamides as pharmaceutical agents and in pharmaceutical compositions.

Mucositis is defined as inflammation and/or ulceration of a mucous membrane in the digestive tract. Mucositis can occur in the stomach, intestines and mouth. The disorder is characterized by breakdown of mucosa, which results in redness, swelling and/or the formation of ulcerative lesions.

Oral mucositis is a common dose-limiting toxicity of drug and radiation therapy for cancer; it occurs to some degree in more than one third of all patients receiving anti-neoplastic drug therapy. In granulocytopenic patients, the ulcerations that accompany mucositis are frequent portals of entry for indigenous oral bacteria leading to sepsis or bacteremia. There are about one million occurrences of oral mucositis annually in the United States. Mucositis also includes mucositis that develops spontaneously in a healthy patient not receiving ant-cancer therapy, as in the case of a canker sore or mouth ulcer. Improved therapies to treat mucositis are needed.

Surgical site infection (SSI) is an infection associated with a surgical procedure. Postoperative SSIs are a major source of illness, and less commonly death, in surgical patients (Nichols R L, 2001). The *Guideline for Prevention of Surgical Site Infection* (1999) sets forth recommendations for preventing SSIs.

- Preoperative measures including proper preparation of the patient, antisepsis for surgical team, management of surgical personnel who exhibit signs of transmissible infectious illness, and antimicrobial prophylaxis.
- Intra-operative measures including proper ventilation in the operating room, cleaning and disinfecting of surfaces in the surgical environment, microbiologic sampling, sterilization of surgical instruments, proper surgical attire and drapes, and proper asepsis and surgical technique.
- Proper incision care post-operation, including sterile dressings and hand washing before and after dressing changes.
- Continued surveillance of the surgical wound during the healing process.

Despite these recommendations, SSIs develop in about 1 to 3 of every 100 patients who have surgery (CDC.gov, 2011). These infections can result in major complications that increase the costs and duration of post-operative hospital stays. Accordingly, novel approaches to mitigating SSIs are needed.

Cystic fibrosis (CF) is a genetic disease caused by a mutation in the cystic fibrosis transmembrane conductor regulator (CFTR) that results in abnormally thick and sticky mucus (Yu Q, et al., 2012). The thick, sticky mucus of a CF patient leads to compromised mucus clearance and lung infection. Chronic airway infections are one of the most common and debilitating manifestations of CF (Tümmler B and C Kiewitz, 1999). The stagnant mucus becomes a breeding ground for bacteria like *Pseudomonas aeruginosa*, which causes chronic airway infections (Moreau-Marquis S, G A O'Toole and B A Stanton, 2009). Despite the use of traditional antibacterial therapies in CF patients, most CF patients are afflicted with a chronic *P. aeruginosa* infection as teenagers and adults, leading to increased morbidity and mortality (Hoiby N, B Frederiksen B, T Pressler, 2005). In chronic *P. aeruginosa* infection, the *P. aeruginosa* forms biofilms, resulting in a greater tolerance to antibiotics and increasing difficulty in treatment (Yu Q, et al., 2012). Effective, novel treatments to assuage the effects of bacterial infection and biofilm formation in CF patients are needed.

DEFINITIONS

As used herein, the term "amino" means a functional group having a nitrogen atom and 1 to 2 hydrogen atoms. "Amino" generally may be used herein to describe a primary, secondary, or tertiary amine, and those of skill in the art will readily be able to ascertain the identification of which in view of the context in which this term is used in the present disclosure. The term "amine" or "amine group" or "ammonia group" means a functional group containing a nitrogen atom derived from ammonia ($NH_3$). The amine groups may be primary amines, meaning the nitrogen is bonded to two hydrogen atoms and one substituent group comprising a substituted or unsubstituted alkyl or aryl group or an aliphatic or aromatic group. The amine groups may be secondary amines meaning, the nitrogen is bonded to one hydrogen atom and two substituent groups comprising a substituted or unsubstituted aklyl or aryl groups or an aliphatic or aromatic group, as defined below. The amine groups may be tertiary amines meaning the nitrogen is bonded to three substituent groups comprising a substituted or unsubstituted aklyl or aryl groups or an aliphatic or aromatic group. The amine groups may also be quaternary amines meaning the designated amine group is bonded to a fourth group, resulting in a positively charged ammonium group.

As used herein, the term "amide group" means a functional group comprising a carbonyl group linked to a nitrogen. A "carbonyl group" means a functional group comprising a carbon atom double bonded to an oxygen atom, represented by (C=O).

The term "alkane" means a saturated hydrocarbon, bonded by single bonds. Alkanes can be linear or branched. "Cycloalkanes" are saturated hydrocarbons rings bonded by single bonds.

As used herein, the term "($C_1$-$C_{10}$)alkyl" means a saturated straight chained or branched or cyclic hydrocarbon consisting essentially of 1 to 10 carbon atoms and a corresponding number of hydrogen atoms. Typically straight chained or branched groups have from one to ten carbons, or more typically one to five carbons. Exemplary ($C_1$-$C_{10}$)alkyl groups include methyl (represented by —$CH_3$), ethyl (represented by —$CH_2$—$CH_3$), n-propyl, isopropyl, n-butyl, isobutyl, etc.

Other ($C_1$-$C_{10}$)alkyl groups will be readily apparent to those of skill in the art given the benefit of the present disclosure.

As used herein, the term "($C_2$-$C_9$)heteroalkyl" means a saturated straight chained or branched or cyclic hydrocarbon consisting essentially of 2 to 10 atoms, wherein 2 to 9 of the atoms are carbon and the remaining atom(s) is selected from the group consisting of nitrogen, sulfur, and oxygen. Exemplary ($C_2$-$C_9$)heteroalkyl groups will be readily apparent to those of skill in the art given the benefit of the present disclosure.

As used herein, the term "($C_3$-$C_{10}$)cycloalkyl" means a nonaromatic saturated hydrocarbon group, forming at least one ring consisting essential of 3 to 10 carbon atoms and a corresponding number of hydrogen atoms. ($C_3$-$C_{10}$)cycloalkyl groups can be monocyclic or multicyclic. Individual rings of multicyclic cycloalkyl groups can have different connectivities, for example, fused, bridged, spiro, etc., in addition to covalent bond substitution. Exemplary ($C_3$-$C_{10}$)cycloalkyl groups include cyclopropyl, cyclobutyl, cyclopentyl, cyclohexyl, norbomanyl, bicyclo-octanyl, octahydro-pentalenyl, spiro-decanyl, cyclopropyl substituted with cyclobutyl, cyclobutyl substituted with cyclopentyl, cyclohexyl substituted with cyclopropyl, etc. Other ($C_3$-$C_{10}$)cycloalkyl groups will be readily apparent to those of skill in the art given the benefit of the present disclosure.

As used herein, the term "($C_2$-$C_9$)heterocycloalkyl" means a nonaromatic group having 3 to 10 atoms that form at least one ring, wherein 2 to 9 of the ring atoms are carbon and the remaining ring atom(s) is selected from the group consisting of nitrogen, sulfur, and oxygen. ($C_2$-$C_9$)heterocycloalkyl groups can be monocyclic or multicyclic. Individual rings of such multicyclic heterocycloalkyl groups can have different connectivities, for example, fused, bridged, spiro, etc., in addition to covalent bond substitution. Exemplary ($C_2$-$C_9$) heterocycloalkyl groups include pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo [3.2.1]octanyl, 3-azabicyclo[3.2.1]octanyl, 3,8-diazabicyclo [3.2.1]octanyl, 2,5-diazabicyclo[2.2.1]heptanyl, 2,5-diazabicyclo[2.2.2]octanyl, octahydro-2H-pyrido[1,2-a] pyrazinyl, 3-azabicyclo[4.1.0]heptanyl, 3-azabicyclo[3.1.0] hexanyl, 2-azaspiro[4.4]nonanyl, 7-oxa-1-aza-spiro[4.4] nonanyl, 7-azabicyclo[2.2.2]heptanyl, octahydro-1H-indolyl, etc. The ($C_2$-$C_9$)heterocycloalkyl group is typically attached to the main structure via a carbon atom or a nitrogen atom. Other ($C_2$-$C_9$)heterocycloalkyl groups will be readily apparent to those of skill in the art given the benefit of the present disclosure.

The term "aliphatic group" or "aliphatic" means a nonaromatic group consisting of carbon and hydrogen, and may optionally include one or more double and/or triple bonds. An aliphatic group may be straight chained, branched or cyclic and typically contains between about one and about 24 carbon atoms.

The term "aryl group" may be used interchangeably with "aryl," "aryl ring," "aromatic," "aromatic group," and "aromatic ring." Aryl groups include carbocyclic aromatic groups, typically with six to fourteen ring carbon atoms. Aryl groups also include heteroaryl groups, which typically have five to fourteen ring atoms with one or more heteroatoms selected from nitrogen, oxygen and sulfur.

As used herein, the term "($C_6$-$C_{14}$)aryl" means an aromatic functional group having 6 to 14 carbon atoms that form at least one ring.

As used herein, the term "($C_2$-$C_9$)heteroaryl" means an aromatic functional group having 5 to 10 atoms that form at least one ring, wherein 2 to 9 of the ring atoms are carbon and the remaining ring atom(s) is selected from the group consisting of nitrogen, sulfur, and oxygen. ($C_2$-$C_9$)heteroaryl groups can be monocyclic or multicyclic. Individual rings of such multicyclic heteroaryl groups can have different connectivities, for example, fused, etc., in addition to covalent bond substitution. Exemplary ($C_2$-$C_9$)heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b] thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl, etc. The ($C_2$-$C_9$)heteroaryl group is typically attached to the main structure via a carbon atom, however, those of skill in the art will realize when certain other atoms, for example, hetero ring atoms, can be attached to the main structure. Other ($C_2$-$C_9$)heteroaryl groups will be readily apparent to those of skill in the art given the benefit of the present disclosure.

As used herein, the term "alkyl amine" means an ($C_1$-$C_{10}$) alkyl containing a primary, secondary, or tertiary amine group in place of one hydrogen atom, represented by ($C_1$-$C_{10}$)alkyl amine and (($C_1$-$C_{10}$)alkyl)$_2$ amine.

The term "alkyl ester" means a ($C_1$-$C_{10}$)alkyl containing an ester group in place of one hydrogen atom, represented by —O(O)C—($C_1$-$C_{10}$)alkyl.

The term "alkyl acid" means an ($C_1$-$C_{10}$)alkyl containing a carboxylic acid group in place of one hydrogen atom, represented by ($C_1$-$C_{10}$)alkyl-COOH.

The term "aliphatic acid" means an acid of nonaromatic hydrocarbons, represented by ($C_3$-$C_{10}$)cycloalkyl-COOH.

The term "halo" means a fluorine (F), chlorine (Cl), bromine (Br), iodine (I), or astatine (At) ion.

The term "methoxy" means a ($C_1$)alkyl containing an oxygen in place of one hydrogen atom, represented by —(O) $CH_3$.

The term "polyol" means an alcohol containing multiple hydroxyl (—OH) groups.

"Substituted" means the substitution of a carbon in alkyl, heterocyclic or aryl groups with one or more non-carbon substituent. Non-carbon substituents are selected from nitrogen, oxygen and sulfur.

"Unsubstituted" means the group is comprised of only hydrogen and carbon.

The term "polymer" means a molecule comprised of repeating units. The term "repeat unit" or "monomer" means a group in a polymer that repeats or appears multiple times in a polymer. A polymer may be a copolymer if the repeating units or "comonomers" are chemically and structurally different from one another.

The term "pharmaceutically acceptable anion" means an anion that is suitable for pharmaceutical use. Pharmaceutically acceptable anions include but are not limited to halides, carbonate, bicarbonate, sulfate, bisulfate, hydroxide, nitrate, persulfate, sulfite, acetate, ascorbate, benzoate, citrate, dihydrogen citrate, hydrogen citrate, oxalate, succinate, tartrate, taurocholate, glycocholate, and cholate.

The term "pharmaceutically acceptable end group" means an end group that is suitable for pharmaceutical use. Examples of pharmaceutically acceptable end groups include but are not limited to H, $(C_1$-$C_{10})$alkyl, $(C_2$-$C_9)$heteroalkyl, $(C_3$-$C_{10})$cycloalkyl, $(C_2$-$C_9)$heterocycloalkyl, $(C_6$-$C_{14})$aryl, $(C_2$-$C_9)$heteroaryl, $(C_1$-$C_{10})$alkylamine, —O(O)C—$(C_1$-$C_{10})$alkyl, $(C_1$-$C_{10})$alkyl-COOH, $(C_3$-$C_{10})$cycloalkyl-COOH, —(O)$CH_3$, —OH, amide, a guanidino group, a guanidinium chloride group, a guanidinobenzene group, a dihydroxy group, and a polyethylene glycol group.

A "guanidino group" is represented by Formula (A):

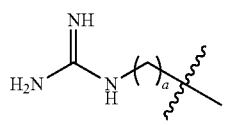

(A)

wherein a is an integer from 0 to 25,

A "guanidinium chloride group" is represented by Formula (B),

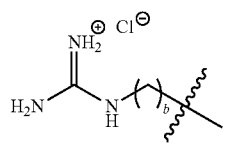

(B)

wherein b is an integer from 0 to 25,

A "guanidinobenzene group" is represented by Formula (C),

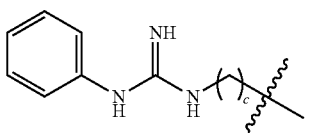

(C)

wherein c is an integer from 0 to 25,

A "dihydroxy group" is represented by Formula (D),

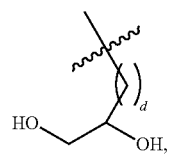

(D)

wherein d is an integer from 0 to 25, or

A "polyethylene glycol group" is represented by Formula (E)

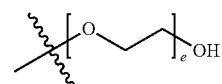

(E)

wherein e is an integer from 1 to 400.

The term "effective amount" of a disclosed amine functional polyamides is a quantity sufficient to achieve a therapeutic and/or prophylactic effect on the particular condition being treated, such as an amount which results in the prevention or a decrease in the symptoms associated with mucositis, oral mucositis, infection and surgical site infection, and lung infection associated with cystic fibrosis. The precise amount of the disclosed amine functional polyamides that is administered will depend on the type and severity of mucositis or infection being treated and on the characteristics of the individual, such as general health, age, sex, body weight and tolerance to drugs.

RELATED ART

Not applicable

BRIEF SUMMARY OF THE INVENTION

In one aspect of the invention, the amine functional polyamides are a compound comprising the structure of Formula (I):

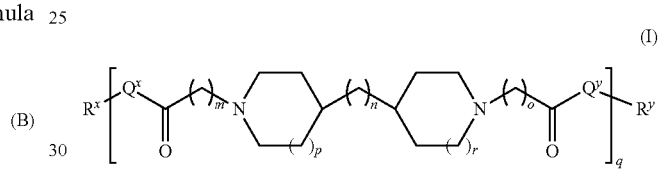

(I)

wherein:
i) m is 0, 1, 2, or 3;
ii) n is 0, 1, 2, or 3;
iii) o is 0, 1, 2, or 3;
iv) p is 0 or 1;
v) r is 0 or 1;
vi) q is an integer from 1 to 400;
vii) $Q^x$ is NH, $(C_1$-$C_{10})$alkyl, $(C_2$-$C_9)$heteroalkyl, $(C_3$-$C_{10})$cycloalkyl, $(C_2$-$C_9)$heterocycloalkyl, $(C_6$-$C_{14})$aryl, $(C_2$-$C_9)$heteroaryl;
viii) $Q^y$ is NH—$R^w$, $(C_1$-$C_{10})$alkyl, or $(C_6$-$C_{14})$aryl, wherein $R^w$ is absent or a $(C_1$-$C_{10})$alkyl, $(C_2$-$C_9)$heteroalkyl, $(C_6$-$C_{14})$aryl, or $(C_2$-$C_9)$heteroaryl;
ix) $R^x$ and $R^y$ are each independently a pharmaceutically acceptable end group.

In another aspect of the invention, the amine functional polyamides are a compound comprising the structure of Formula (II):

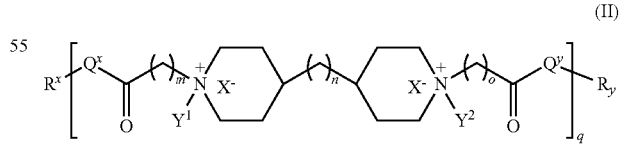

(II)

wherein:
i) m is 0, 1, 2, or 3;
ii) n is 0, 1, 2, or 3;
iii) o is 0, 1, 2, or 3;
iv) p is 0 or 1;
v) r is 0 or 1;
vi) q is an integer from 1 to 400;

vii) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;

viii) $Q^y$ is NH—$R^w$, NH—CH$_2$—$R_w$, $(C_1-C_{10})$alkyl, or $(C_6-C_{14})$aryl, wherein $R^w$ is absent or a $(C_1-C_{10})$alkyl, $(C_2-C_9)$heteroalkyl, $(C_6-C_{14})$aryl, or $(C_2-C_9)$heteroaryl;

ix) $R^x$ and $R^y$ are each independently a pharmaceutically acceptable end group;

x) $X^-$ is each independently a halo or any pharmaceutically acceptable anion;

xi) $Y^1$ and $Y^2$ are each independently H or $(C_1-C_{10})$alkyl optionally substituted by one or more substituents selected from the group consisting of $(C_1-C_{10})$alkyl, $(C_2-C_9)$heteroalkyl, $(C_3-C_{10})$cycloalkyl, $(C_2-C_9)$heterocycloalkyl, $(C_1-C_{14})$aryl, $(C_2-C_9)$heteroaryl, $(C_1-C_{10})$alkylamine, —O(O)C—$(C_1-C_{10})$alkyl, —$(C_1-C_{10})$alkyl-COOH, $(C_3-C_{10})$cycloalkyl-COON, —(O)CH$_3$, —OH, amide, a dihydroxy group, represented by Formula (D),

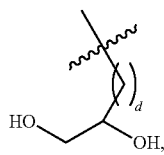
(D)

wherein d is an integer from 0 to 25, or
a polyethylene glycol group, represented by Formula (E)

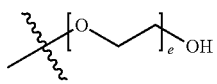
(E)

wherein e is an integer from 1 to 25.

In yet another aspect of the invention, the amine functional polyamides are a compound comprising the structure of Formula (III):

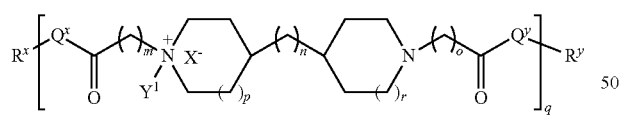
(III)

wherein:
i) m is 0, 1, 2, or 3;
ii) n is 0, 1, 2, or 3;
iii) o is 0, 1, 2, or 3;
iv) p is 0 or 1;
v) r is 0 or 1;
vi) q is an integer from 1 to 400;
vii) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_1-C_{10})$aryl, $(C_2-C_9)$heteroaryl;
viii) $Q^y$ is NH—$R^w$, NH—CH$_2$—$R_w$, $(C_1-C_{10})$alkyl, or $(C_6-C_{14})$aryl, wherein $R^w$ is absent or a $(C_1-C_{10})$alkyl, $(C_2-C_9)$heteroalkyl, $(C_6-C_{14})$aryl, or $(C_2-C_9)$heteroaryl;

i) $R^x$ and $R^y$ are each independently a pharmaceutically acceptable end group;

ix) $X^-$ is a halo or any pharmaceutically acceptable anion;

x) $Y^1$ is H or $(C_1-C_{10})$alkyl optionally substituted by one or more substituents selected from the group consisting of $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, —S—O—$(C_1-C_{10})$alkyl, —O(O)C—$(C_1-C_{10})$alkyl, —$(C_1-C_{10})$alkyl-COOH, $(C_3-C_{10})$cycloalkyl-COOH, —(O)CH$_3$, —OH, amide, a dihydroxy group, represented by Formula (D),

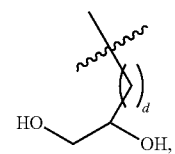
(D)

wherein d is an integer from 0 to 25, or
a polyethylene glycol group, represented by Formula (E),

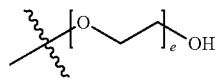
(E)

wherein e is an integer from 1 to 400.

In another aspect of the invention, the amine functional polyamides are a compound comprising the structure of Formula (IV):

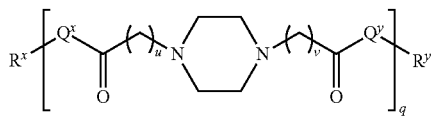
(IV)

wherein:
i) u is 0, 1, 2, or 3;
ii) v is 0, 1, 2, or 3;
iii) q is an integer from 1 to 400;
iv) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
v) $Q^y$ is NH—$R^w$, NH—CH$_2$—$R_w$, $(C_1-C_{10})$alkyl, or $(C_6-C_{14})$aryl, wherein $R^w$ is absent or a $(C_1-C_{10})$alkyl, $(C_2-C_9)$heteroalkyl, $(C_1-C_{14})$aryl, or $(C_2-C_9)$heteroaryl;
vi) $R^x$ and $R^y$ are each independently a pharmaceutically acceptable end group.

In yet another aspect of the invention, the amide functional polyamides are a compound comprising the structure of Formula (V):

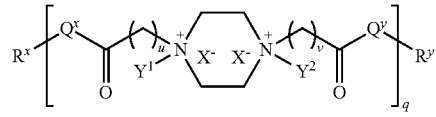
(V)

wherein:
i) u is 0, 1, 2, or 3;
ii) v is 0, 1, 2, or 3;
iii) q is an integer from 1 to 400;
iv) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
v) $Q^y$ is NH—$R^w$, NH—CH$_2$—$R_w$, $(C_1-C_{10})$alkyl, or $(C_6-C_{14})$aryl, wherein $R^w$ is absent or a $(C_1-C_{10})$alkyl, $(C_2-C_9)$heteroalkyl, $(C_6-C_{14})$aryl, or $(C_2-C_9)$heteroaryl;
vi) $R^x$ and $R^y$ are each independently a pharmaceutically acceptable end group;
vii) $X^-$ is independently a halo or any pharmaceutically acceptable anion,
viii) $Y^1$ and $Y^2$ are independently H or $(C_1-C_{10})$alkyl optionally substituted by one or more substituents selected from the group consisting of $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, —O(O)C—$(C_1-C_{10})$alkyl, —$(C_1-C_{10})$alkyl-COOH, $(C_3-C_{10})$cycloalkyl-COOH, —(O)CH$_3$, —OH, amide, a dihydroxy group, represented by Formula (D),

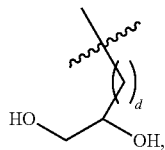

(D)

wherein d is an integer from 0 to 25, or
a polyethylene glycol group, represented by Formula (E)

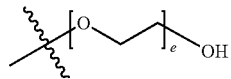

(E)

wherein e is an integer from 1 to 400.

In one aspect of the invention, the amine functional polyamides are a pharmaceutical composition comprising a compound comprising the structure of Formula (I). In another aspect of the invention, amine functional polyamides are a pharmaceutical composition comprising a compound comprising the structure of Formula (II). In yet another aspect of the invention, amine functional polyamides are a pharmaceutical composition comprising a compound comprising the structure of Formula (III). In another aspect of the invention, amine functional polyamides are a pharmaceutical composition comprising a compound comprising the structure of Formula (IV). In another aspect of the invention, amine functional polyamides are a pharmaceutical composition comprising a compound comprising the structure of Formula (V).

In one aspect of the invention, the amine functional polyamides are used for the treatment of mucositis. In another aspect of the invention, the amine functional polyamides are used for the treatment of oral mucositis. In another embodiment of the invention, the amine functional polyamides are used for the treatment of an infection. In yet another embodiment of the invention, the amine functional polyamides are used for the treatment of surgical site infection. In another embodiment of the invention, the amine functional polyamides are used for the treatment of lung infection associated with cystic fibrosis. In another embodiment of the invention, the amine functional polyamides are used for the treatment of P. aeruginosa lung infections in CF patients. In yet another embodiment of the invention, the amine functional polyamides are used for the treatment of P. aeruginosa lung infections in CF patients where biofilms have formed. Yet another aspect of the invention is a method of treating a condition selected from mucositis, oral mucositis, and infection comprising administering an amine functional polyamide.

BRIEF DESCRIPTION OF THE SEVERAL VIEWS OF THE DRAWINGS

FIG. 1 shows a comparison of the susceptibility of Pseudomonas Aeruginosa present in biofilm of cystic fibrosis-derived human airway epithelial cells of representative amine functional polyamide. The columns (left to right) show the mean log$_{10}$ CFU (colony forming units) observed for untreated control cystic fibrosis bronchial epithelial (CFBE) cells, CFBE cells treated with 50 μg/mL tobramycin, CFBE cells treated with 50 μg/mL poly(4,4-trimethylene dipiperidinebisporpanoic acid-diaminopropane), and CFBE cells treated with 500 μg/mL poly(4,4-trimethylene dipiperidinebisporpanoic acid-diaminopropane) according to the in vitro study described in Example 1-5.

DETAILED DESCRIPTION OF THE INVENTION

This invention relates to novel amine functional polyamides. The amine functional polyamides polymers or copolymers and are of varying structures and comprise amine and ammonium groups along the polymer chain.

The amine functional polyamides contain repeat units of amide groups and amine groups; the amine groups can be secondary, tertiary, and quaternary ammonium groups.

Further, the amine functional polyamides of the present invention are of varying molecular weights.

The amine functional polyamides are water soluble.

This invention relates to pharmaceutical compositions comprising polymers or copolymers of amine functional polyamides. This invention also relates to methods of treating and preventing mucositis and infection, including SSI, lung infections in CF patients, and C. aeruginosa lung infections in CF patients with or without biofilm formation, with amine functional polyamides. The amine functional polyamides and the pharmaceutical compositions comprising polymers or copolymers of amine functional polyamides can be administered in multiple dosage forms and for systemic or local administration.

This invention relates to the use of amine functional polyamides and pharmaceutical compositions comprising polymers or copolymers of amine functional polyamides as anti-infective agents. The amine functional polyamides and pharmaceutical compositions comprising polymers or copolymers of amine functional polyamides can be used for the treatment of bacterial, fungal, and viral infections, including mucositis, infections and, specifically, surgical site infections, lung infections associated with CF, and C. aeruginosa lung infections in CF patients with or without biofilm formation.

The amine functional polyamides can also be used to coat surfaces of various biomedical devices and other surfaces to prevent infection.

In one aspect of the invention, the amine functional polyamides are a compound comprising the structure of Formula (I):

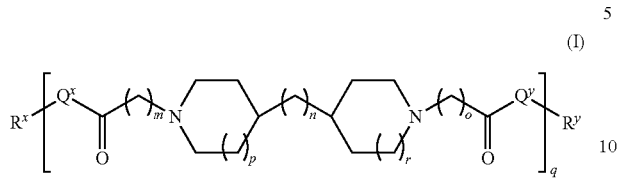

(I)

wherein:
i) m is 0, 1, 2, or 3;
ii) n is 0, 1, 2, or 3;
iii) o is 0, 1, 2, or 3;
iv) p is 0 or 1;
v) r is 0 or 1;
vi) q is an integer from 1 to 400;
vii) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
viii) $Q^y$ is NH—$R_w$, $(C_1-C_{10})$alkyl, or $(C_6-C_{14})$aryl, wherein $R^w$ is absent or a $(C_1-C_{10})$alkyl, $(C_2-C_9)$heteroalkyl, $(C_6-C_{14})$aryl, or $(C_2-C_9)$heteroaryl;
ix) $R^x$ and $R^y$ are each independently a pharmaceutically acceptable end group.

In another aspect of the invention, the amine functional polyamides are a compound comprising the structure of Formula (II):

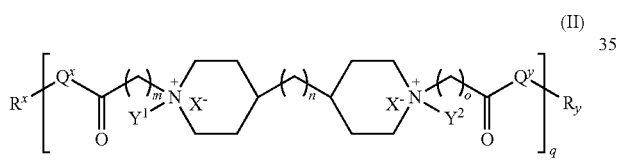

(II)

wherein:
i) m is 0, 1, 2, or 3;
ii) n is 0, 1, 2, or 3;
iii) o is 0, 1, 2, or 3;
iv) p is 0 or 1;
v) r is 0 or 1;
vi) q is an integer from 1 to 400;
vii) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
viii) $Q^y$ is NH—$R^w$, NH—$CH_2$—$R_w$, $(C_1-C_{10})$alkyl, or $(C_6-C_{14})$aryl, wherein $R^w$ is absent or a $(C_1-C_{10})$alkyl, $(C_2-C_9)$heteroalkyl, $(C_6-C_{14})$aryl, or $(C_2-C_9)$heteroaryl;
ix) $R^x$ and $R^y$ are each independently a pharmaceutically acceptable end group;
x) $X^-$ is each independently a halo or any pharmaceutically acceptable anion;
xi) $Y^1$ and $Y_2$ are each independently H or $(C_1-C_{10})$alkyl optionally substituted by one or more substituents selected from the group consisting of $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, —O(O)C—$(C_1-C_{10})$alkyl, —$(C_1-C_{10})$alkyl-COOH, $(C_3-C_{10})$cycloalkyl-COOH, —$(O)CH_3$, —OH, amide, a dihydroxy group, represented by Formula (D),

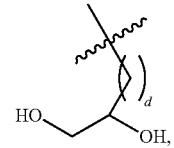

(D)

wherein d is an integer from 0 to 25, or
a polyethylene glycol group, represented by Formula (E)

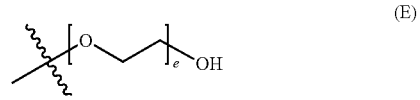

(E)

wherein e is an integer from 1 to 25.

In yet another aspect of the invention, the amine functional polyamides are a compound comprising the structure of Formula (III)

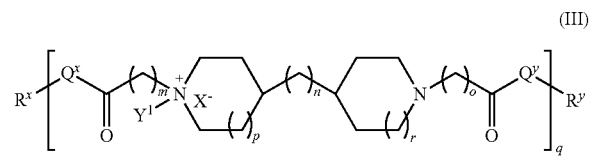

(III)

wherein:
i) m is 0, 1, 2, or 3;
ii) n is 0, 1, 2, or 3;
iii) o is 0, 1, 2, or 3,
iv) p is 0 or 1;
v) r is 0 or 1;
vi) q is an integer from 1 to 400;
vii) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
viii) $Q^y$ is NH—$R^w$, NH—$CH_2$—$R_w$, $(C_1-C_{10})$alkyl, or $(C_5-C_{14})$aryl, wherein $R^w$ is absent or a $(C_1-C_{10})$alkyl, $(C_2-C_9)$heteroalkyl, $(C_6-C_{14})$aryl, or $(C_2-C_9)$heteroaryl;
ii) $R^x$ and $R^y$ are each independently a pharmaceutically acceptable end group;
ix) $X^-$ is a halo or any pharmaceutically acceptable anion;
x) $Y^1$ is H or $(C_1-C_{10})$alkyl optionally substituted by one or more substituents selected from the group consisting of $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, —S—O—$(C_1-C_{10})$alkyl, —O(O)C—$(C_1-C_{10})$alkyl, —$(C_1-C_{10})$alkyl-COOH, $(C_3-C_{10})$cycloalkyl-COOH, —$(O)CH_3$, —OH, amide, a dihydroxy group, represented by Formula (D),

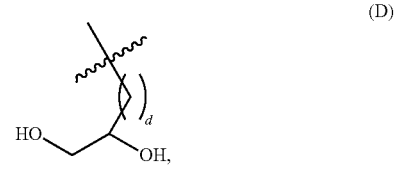

(D)

wherein d is an integer from 0 to 25, or
a polyethylene glycol group, represented by Formula (E),

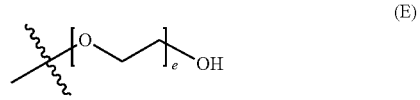

(E)

wherein e is an integer from 1 to 400.

In preferred embodiments of the invention, the amine functional polyamides of are compounds of Formula (I), Formula (II) or Formula (III) where p and r are both 0 and p and r are both 1. In other preferred embodiments of the invention, the amine functional polyamides of are compounds of Formula (I), Formula (II) or Formula (III) where n, p and r are all 0, n is 0 and p and r are both 1, and n is 3 and p and r are both 1.

In a preferred embodiment of the invention, the amide functional polyamides are a compound comprising the structure of Formula (1).

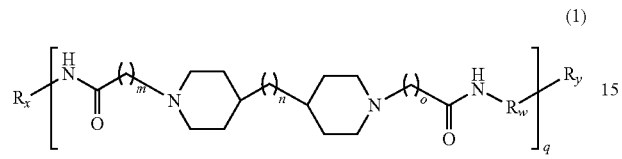

(1)

wherein $R^w$ is a $(C_1-C_{10})$alkyl, $(C_2-C_9)$heteroalkyl, $(C_6-C_{14})$aryl, or $(C_2-C_9)$heteroaryl.

In another preferred embodiment of the invention, the amide functional polyamides are a compound comprising the structure of Formula (2) or Formula (3):

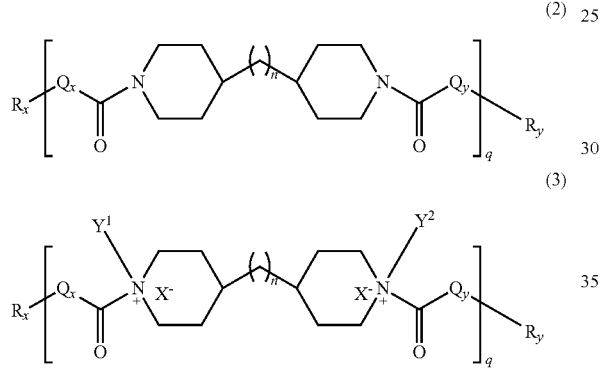

(2)

(3)

In yet another preferred embodiment of the invention, the amine functional polyamides are comprised of a compound comprising the structure of Formula (I), Formula (II), Formula (III), Formula (1), Formula (2) or Formula (3), wherein $R^x$ and $R^y$ are independently selected from a methoxy group, a guanidino group, or a guanidinobenzene group.

In another aspect of the invention, the amine functional polyamides are a compound comprising the structure of Formula (IV):

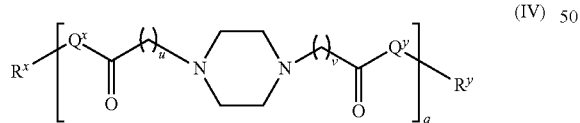

(IV)

wherein:
i) u is 0, 1, 2, or 3;
ii) v is 0, 1, 2, or 3;
iii) q is an integer from 1 to 400;
iv) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
v) $Q^y$ is NH—$R^w$, NH—CH$_2$—$R_w$, $(C_1-C_{10})$alkyl, or $(C_6-C_{14})$aryl, wherein $R^w$ is absent or a $(C_1-C_{10})$alkyl, $(C_2-C_9)$heteroalkyl, $(C_6-C_{14})$aryl, or $(C_2-C_9)$heteroaryl;
vii) $R^x$ and $R^y$ are each independently a pharmaceutically acceptable end group.

In yet another aspect of the invention, the amide functional polyamides are a compound comprising the structure of Formula (V):

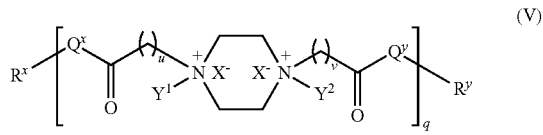

(V)

wherein:
i) u is 0, 1, 2, or 3;
ii) v is 0, 1, 2, or 3;
iii) q is an integer from 1 to 400;
iv) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
v) $Q^y$ is NH—$R^w$, NH—CH$_2$—$R_w$, $(C_1-C_{10})$alkyl, or $(C_6-C_{14})$aryl, wherein $R^w$ is absent or a $(C_1-C_{10})$alkyl, $(C_2-C_9)$heteroalkyl, $(C_6-C_{14})$aryl, or $(C_2-C_9)$heteroaryl;
vii) $R^x$ and $R^y$ are each independently a pharmaceutically acceptable end group;
ix) $X^-$ is independently a halo or any pharmaceutically acceptable anion,
x) $Y^1$ and $Y^2$ are independently H or $(C_1-C_{10})$alkyl optionally substituted by one or more substituents selected from the group consisting of $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, —S—O—$(C_1-C_{10})$alkyl, —O(O)C—$(C_1-C_{10})$alkyl, —$(C_1-C_{10})$alkyl-COOH, $(C_3-C_{10})$cycloalkyl-COOH, —(O)CH$_3$, —OH, amide, a dihydroxy group, represented by Formula (D),

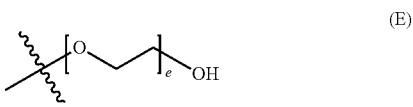

(D)

wherein d is an integer from 0 to 25, or
a polyethylene glycol group, represented by Formula (E)

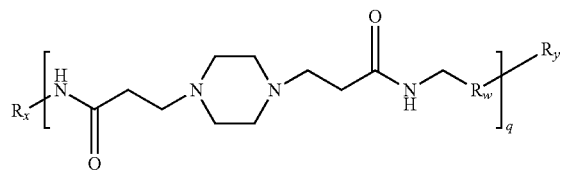

(E)

wherein e is an integer from 1 to 400.

In a preferred embodiment of the invention, the amine functional polyamides of are compounds of Formula (IV) or Formula (V) where u and v are both 2.

In a preferred embodiment of the invention, the amide functional polyamides are a compound comprising the structure of Formula (4).

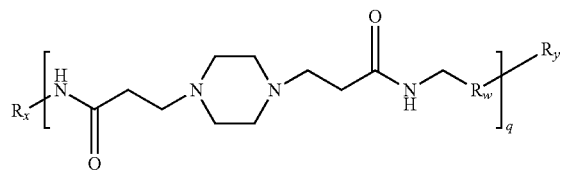

(4)

In one aspect of the invention, the amine functional polyamides are a pharmaceutical composition comprising a compound comprising the structure of Formula (I). In another aspect of the invention, amine functional polyamides are a pharmaceutical composition comprising a compound comprising the structure of Formula (II). In yet another aspect of the invention, amine functional polyamides are a pharmaceutical composition comprising a compound comprising the structure of Formula (III). In preferred embodiments of the invention, the amine functional polyamides are a pharmaceutical composition comprising a compound comprising the structure of Formula (1), Formula (2), or Formula (3). In yet another preferred embodiment of the invention, the amine functional polyamides are a pharmaceutical composition comprising a compound comprising the structure of Formula (I), Formula (II), Formula (III), Formula (1), Formula (2) or Formula (3), wherein $R_x$ and $R_y$ are independently selected from a methoxy group, a guanidino group, or a guanidinobenzene group.

In another aspect of the invention, amine functional polyamides are a pharmaceutical composition comprising a compound comprising the structure of Formula (IV). In another aspect of the invention, amine functional polyamides are a pharmaceutical composition comprising a compound comprising the structure of Formula (V). In a preferred embodiment of the invention, the amine functional polyamides are a pharmaceutical composition comprising a compound comprising the structure of Formula (4).

In another preferred embodiment of the invention, the amine functional polyamides are a pharmaceutical composition comprising a compound comprising the structure of Formula (I), (II), (III), (IV), (V), (1), (2), (3) or (4) for use in the treatment or prevention of a condition selected from mucositis, oral mucositis and infection. In yet another preferred embodiment, the amine functional polyamides are a pharmaceutical composition comprising a compound comprising the structure of Formula (I), (II), (III), (IV), (V), (1), (2), (3) or (4) for use in the treatment or prevention of a surgical site infection, a lung infection associated with cystic fibrosis, a *Pseudomonas aeruginosa* lung infection, and a *Pseudomonas aeruginosa* lung infection where biofilms are present.

In one embodiment of the invention, the amine functional polyamides are polymers. In some embodiments, the polymers may comprise a monomer comprising a compound having a repeat unit according to any of Formulas (I), (II), (III), (IV), (V), (1), (2), (3) or (4).

In one embodiment of the invention, the amine functional polyamides are copolymers. In some embodiments, the copolymers may comprise a monomer comprising a compound having at least one unit according to any of Formulas (I), (II), (III), (IV), (V), (1), (2), (3) or (4) which is copolymerized with one or more other comonomers or oligomers or other polymerizable groups. Non-limiting examples of suitable comonomers which may be used alone or in combination with at least one unit according to any of Formulas (I), (II), (III), (IV), (V), (1), (2), (3) or (4) to form the amine functional polyamides are presented in Table 1.

In one embodiment of the invention, the amine functional polyamides are polymers or copolymers comprised of about 1 to about 400 repeat units according to any of Formulas (I), (II), (III), (IV), (V), (1), (2), (3) or (4). In one aspect of the invention, the amine functional polyamides are polymers or copolymers comprised of about 1 to about 200 repeat units according to any of Formulas (I), (II), (III), (IV), (V), (1), (2), (3) or (4). In another aspect of the invention, the amine functional polyamides are polymers or copolymers comprised of about 1 to about 100 repeat units according to any of Formulas (I), (II), (III), (IV), (V), (1), (2), (3) or (4). In some embodiments, the amine functional polyamides are polymers or copolymers comprised of about 1 to about 50 repeat units according to any of Formulas (I), (II), (III), (IV), (V), (1), (2), (3) or (4). In an additional embodiment, the amine functional polyamides are polymers or copolymers comprised of about 1 to about 25 repeat units according to any of Formulas (I), (II), (III), (IV), (V), (1), (2), (3) or (4). In yet another embodiment, the amine functional polyamides are polymers or copolymers comprised of about 1 to about 10 repeat units according to any of Formulas (I), (II), (III), (IV), (V), (1), (2), (3) or (4). In other embodiments, the amine functional polyamides are polymers or copolymers comprised of about 5 to about 40 repeat units according to any of Formulas (I), (II), (III), (IV), (V), (1), (2), (3) or (4). In one embodiment, the amine functional polyamides are polymers or copolymers comprised of about 5 to about 30 repeat units according to any of Formulas (I), (II), (III), (IV), (V), (1), (2), (3) or (4). In another embodiment, the amine functional polyamides are polymers or copolymers comprised of about 5 to about 25 repeat units according to any of Formulas (I), (II), (III), (IV), (V), (1), (2), (3) or (4). In yet another embodiment, the amine functional polyamides are polymers or copolymers comprised of about 5 to about 10 repeat units according to any of Formulas (I), (II), (III), (IV), (V), (1), (2), (3) or (4).

In one aspect of the invention, the amine functional polyamides have a molecular weight less than about 10,000 g/mol. In another aspect of the invention, the amine functional polyamides have a molecular weight less than about 9,000 g/mol. In an additional aspect of the invention, the amine functional polyamides have a molecular weight less than about 8,000 g/mol. In yet another aspect of the invention, the amine functional polyamides have a molecular weight less than about 7,000 g/mol.

In one aspect of the invention, the amine functional polyamides are optionally, independently terminated ($R^x$ and $R^y$) with a pharmaceutically acceptable end group. Representative examples of pharmaceutically acceptable end groups will be obvious to one of skill in the art, including H, $(C_1-C_{10})$alkyl, $(C_2-C_0)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, —O(O)C—$(C_1-C_{10})$alkyl, $(C_1-C_{10})$alkyl-COOH, $(C_3-C_{10})$cycloalkyl-COOH, —(O)CH$_3$, —OH, amide, a guanidino group represented by Formula (A)

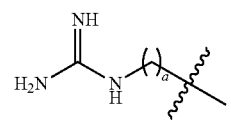

(A)

wherein a is an integer from 0 to 25, a guanidinium chloride group represented by Formula (B),

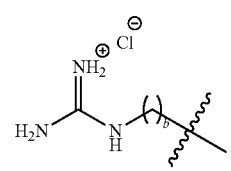

(B)

wherein b is an integer from 0 to 25, a guanidinobenzene group represented by Formula (C),

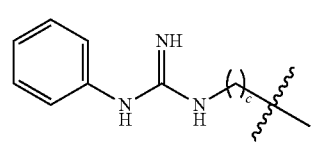

(C)

wherein c is an integer from 0 to 25, a dihydroxy group, represented by Formula (D),

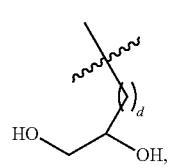
(D)

wherein d is an integer from 0 to 25, or a polyethylene glycol group, represented by Formula (E)

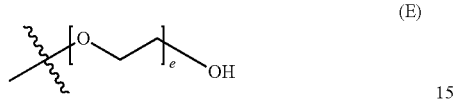
(E)

wherein e is an integer from 1 to 400

The number of repeat units and the molecular weight of the amine functional polyamides are controlled by synthesis of the compound. Methods of preparing preferred amine functional polyamides of the invention and controlling for the number of repeat units and molecular are described in Example 3.

TABLE 1

Amine Functional Polyamides

| Polymer Description | Structure |
|---|---|
| Poly (4,4'-trimethylene dipiperidine bispropanoic acid–N,N'-dimethyl-1,3-diaminopropane) | |
| Poly (4,4'-trimethylene dipiperidine bispropanoic acid-4,4'-trimethylene dipiperidine) | |
| Poly (4,4'-trimethylene dipiperidine bispropanoic acid-piperazine) | |
| Poly(4,4'-trimethylene dipiperidine bispropanoic acid-diaminoethane) Mw <10K | |
| Poly(4,4'-trimethylene dipiperidinebis-propanoic acid-diaminopropane) Mw <10K | |

TABLE 1-continued

Amine Functional Polyamides

| Polymer Description | Structure |
|---|---|
| Poly(4,4-trimethylene dipiperidinebis-propanoic acid-diaminopropane) Mw >10K | 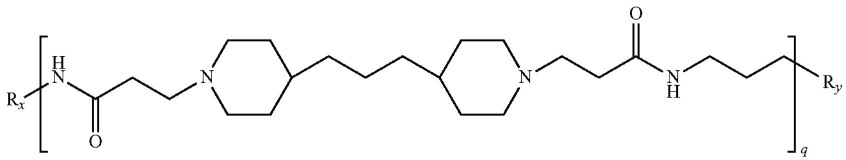 |
| Poly(4,4-trimethylene dipiperidinebis-propanoic acid-diaminopropane) Mw 1650 | 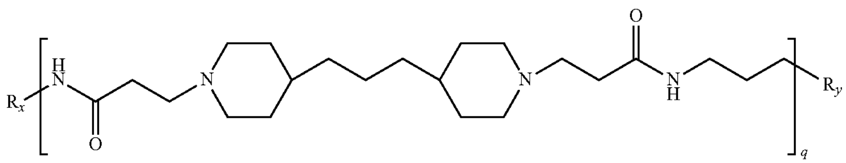 |
| Poly(4,4-trimethylene dipiperidinebis-propanoic acid-diaminopropane) Mw 7.7K | 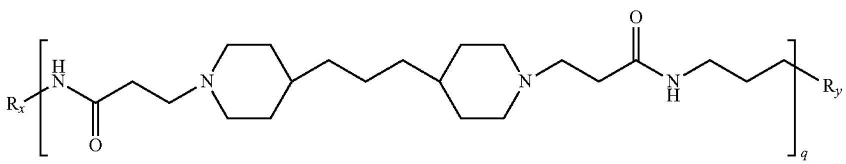 |
| Poly(4,4-trimethylene dipiperidinebis-propanoic acid-diaminopropane) Mw 3K | 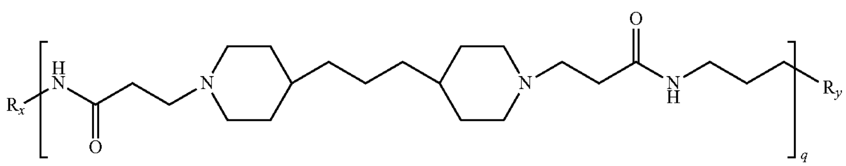 |
| Poly(4,4-trimethylene dipiperidinebis-propanoic acid-diaminopropane) Mw 5K | 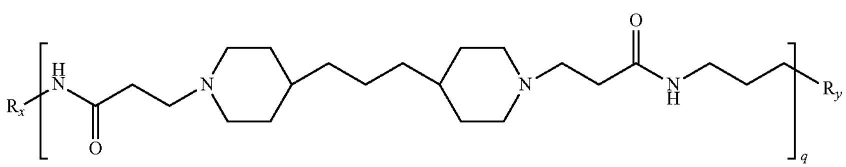 |

TABLE 1-continued

Amine Functional Polyamides

| Polymer Description | Structure |
|---|---|
| Poly(4,4-trimethylene dipiperidinebis-propanoic acid-diaminopropane), Mw 3250 | 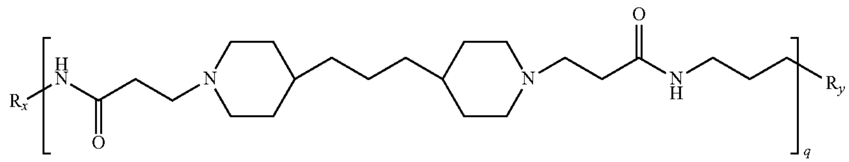 |
| Poly(4,4-trimethylene dipiperidinebis-propanoic acid-diaminopropane), Mw 4700 | 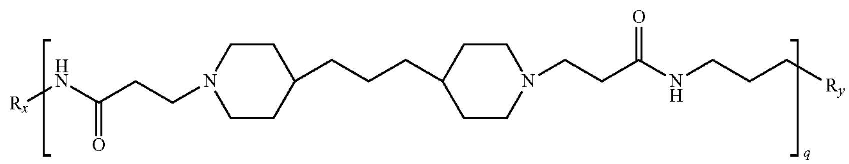 |
| Poly(4,4-trimethylene dipiperidinebis-propanoic acid-diaminopropane), Mw 2500 | 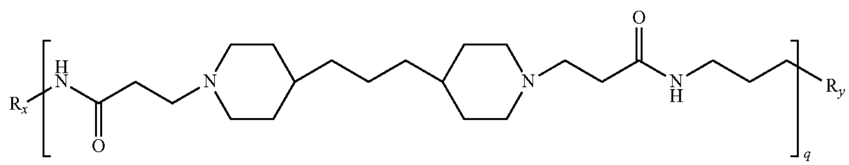 |
| Poly(4,4-trimethylene dipiperidinebis-propanoic acid-diaminopropane) | 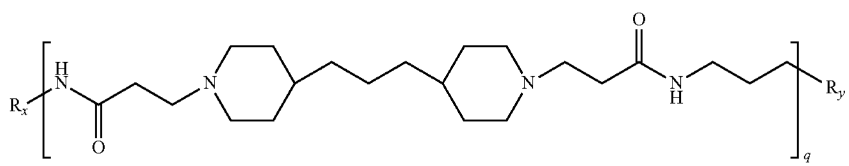 |
| Poly(4,4-trimethylene dipiperidinebis-propanoic acid-diaminopropane) Mw 1400 | 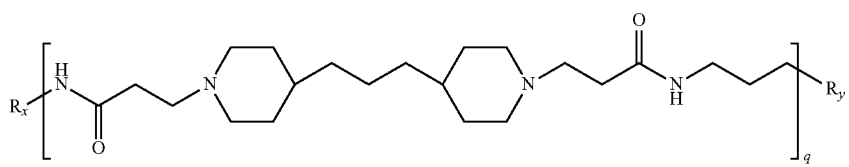 |

TABLE 1-continued

Amine Functional Polyamides

| Polymer Description | Structure |
|---|---|
| Poly(4,4-trimethylene dipiperidinebis-propanoic acid-diaminobutane) Mw <10K | (structure) |
| Poly(4,4-trimethylene dipiperidinebis-propanoic acid-diaminobutane) Mw >10K | (structure) |
| Poly(4,4-trimethylene dipiperidinebis-propanoic acid-diaminotriPEG) Mw <10K | (structure) |
| Poly(4,4-trimethylene dipiperidinebis-propanoic acid-diaminotriPEG) Mw >10K | (structure) |
| Poly(4,4-trimethylene dipiperidinebis-propanoic acid-N(2-aminoethyl)-diaminoethane) | (structure) |
| Poly(4,4-trimethylenedi-piperidinebisprop-anoic acid-2,2'-diamino-diethylamine) Mw 5.5K | (structure) |

TABLE 1-continued

Amine Functional Polyamides

| Polymer Description | Structure |
|---|---|
| Poly(4,4'-trimethylenedipiperidinebispropanoic acid 2,2'-diaminodiethylamine) Mw ~14,000 | |
| Poly(4,4'-trimethylenedipiperidinebispropanoic acid 1,4-benzyldiamine) Mw <10K | |
| Poly(4,4'-trimethylenedipiperidinebispropanoic acid N(3-aminopropyl)1,3-propanediamine) Mw <10K | |
| Poly(4,4'-trimethylenedipiperidinebispropanoic acid 3,3'-diamino-N-methyldipropylamine) Mw <10K | |
| Poly(4,4'-trimethylenedipiperidinebispropanoic acid 2,2'-diamino-N-methyldiethylamine) | |

TABLE 1-continued

Amine Functional Polyamides

| Polymer Description | Structure |
|---|---|
| Poly(piperazine-bispropanoic acid-1,2-bis(2-aminoethoxy)ethane) Mw <10K | 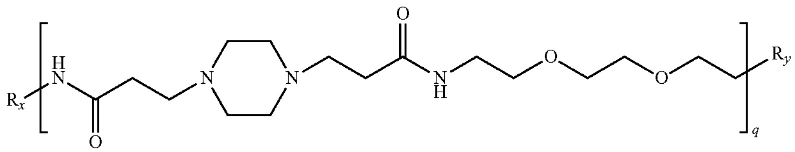 |
| Poly(piperazine-bispropanoic acid-2,2-diaminodiethylamine) Mw <10K | 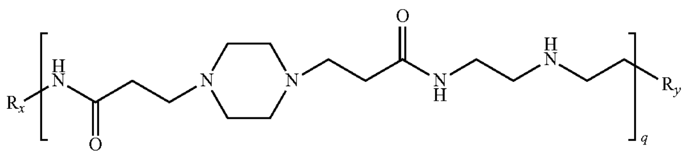 |
| Poly(piperazine-bispropanoic acid-N-methyl-2,2-diaminodiethylamine) Mw <10K | 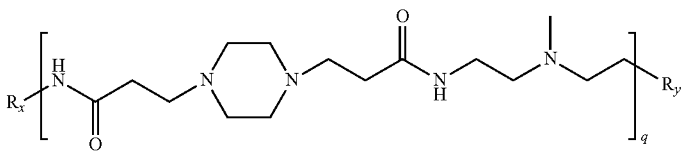 |
| Poly(piperazine-bispropanoic acid-N(3-aminopropyl)1,3-propanediamine) Mw <10K | |
| Poly(piperazine-bispropanoic acid-3,3'-diamino-N-methyl-dipropylamine) Mw <10K | |
| Poly(piperazine-bispropanoic acid-1,3-diaminopropane) Mw ~3,700 | 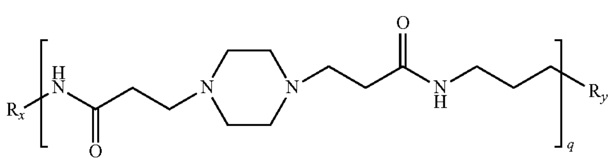 |

TABLE 1-continued

Amine Functional Polyamides

| Polymer Description | Structure |
|---|---|
| Poly(piperazine-bispropanoic acid-1,4-diaminobutane) Mw ~4,400 | 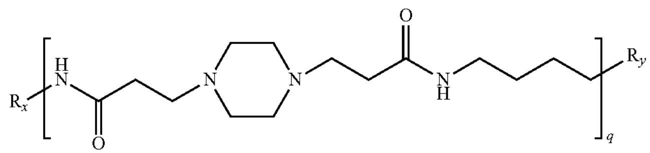 |
| Poly(4,4'-dipiperidinebis-propanoic acid-2,2'-diamino-diethylamine) Mw <5K | 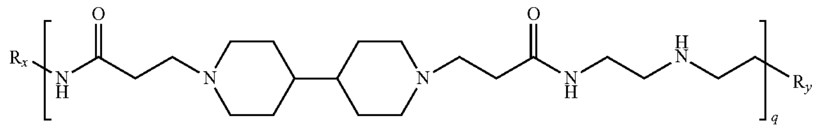 |
| Poly(4,4'-dipiperidinebis-propanoic acid-2,2'-diamino-diethylamine) Mw 5.1K | 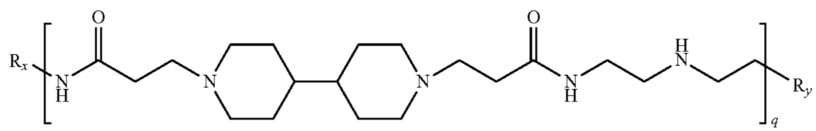 |
| Poly(4,4'-dipiperidinebis-propanoic acid-2,2'-diamino N-methyl diethylamine) Mw <5K | |
| Poly(4,4'-dipiperidinebis-propanoic acid-2,2'-diamino N-methyl diethylamine) Mw <5K | |
| Poly(4,4'-dipiperidinebis-propanoic acid-3,3'-diamino-dipropylamine) Mw <5K | 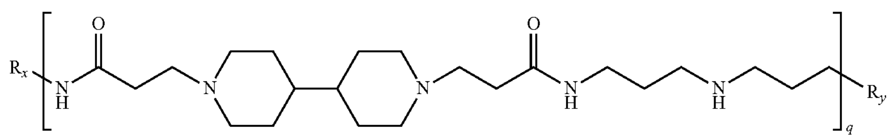 |

TABLE 1-continued

Amine Functional Polyamides

| Polymer Description | Structure |
|---|---|
| Poly(4,4'-dipiperidinebis-propanoic acid-3,3'-diamino-dipropylamine) Mw <5K | 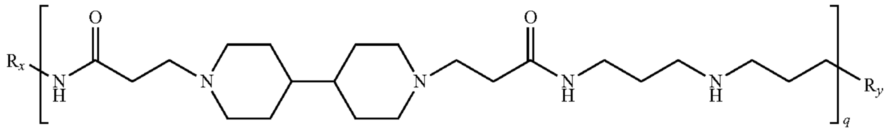 |
| Poly(4,4'-dipiperidinebis-propanoic acid-3,3'-diamino-N-methyl-dipropylamine) Mw ~5 k | |
| Poly(4,4'-dipiperidinebis-propanoic acid-3,3'-diamino-N-methyl-dipropylamine) Mw ~5.5K | 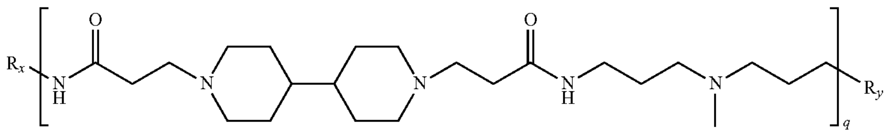 |
| Poly(4,4'-dipiperidinebis-propionic acid-ethylenediamine) Mw <5K | 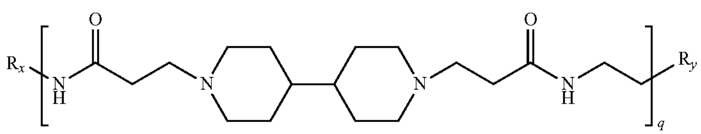 |
| Poly(4,4'-dipiperidinebis-propionic acid-1,3-diaminopropane) Mw <5K | 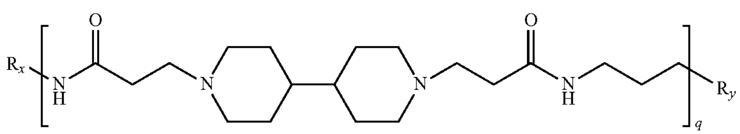 |
| Poly(4,4'-dipiperidinebis-propionic acid-1,4-diaminobutane) Mw <5K | 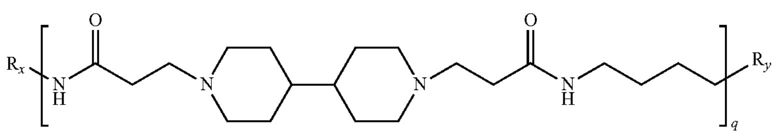 |

TABLE 1-continued

Amine Functional Polyamides

| Polymer Description | Structure |
|---|---|
| Poly(4,4'-trimethylenedipiperidinebispropionic acid-bis(4-aminobutyl)ether) Mw <5K | (structure) |
| Poly(4,4'-trimethylenedipiperidinebispropionic acid-2-dydroxy 1,3-diaminopropane) Mw <5K | (structure) |
| Poly(4,4'-trimethylenedipiperidine-1,3-diaminopropane-N,N'-di-3-propionic acid) Mw <5K | (structure) |
| Poly (4,4' trimethylene dipiperidine bispropanoic acid-N,N'-dimethyl-1,3-diaminopropane), Mw 1K | (structure) |
| Poly(4,4'-trimethylene dipiperidinebis-propanoic acid 4,4'-dipiperidine), Mw 10631 | (structure) |

TABLE 1-continued
Amine Functional Polyamides
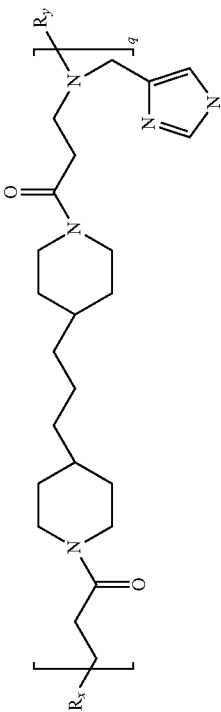

TABLE 1-continued

Amine Functional Polyamides

| Polymer Description | Structure |
|---|---|
| 40 mol % glycidol modified poly(4,4-trimethylene dipiperidinebis-propanoic acid-diaminopropane), Mw 4700 | (structure shown) |

Wherein x is 0.6 and $R_x$ and $R_y$ are HN–CH$_2$–CH(OH)–CH$_2$–OH or NH$_2$.

TABLE 1-continued
Amine Functional Polyamides
| Polymer Description | Structure |
|---|---|
| 40 mol % glycidol modified Poly(4,4-trimethylene dipiperidinebis-propanoic acid-diaminopropane) Mw 5000 | 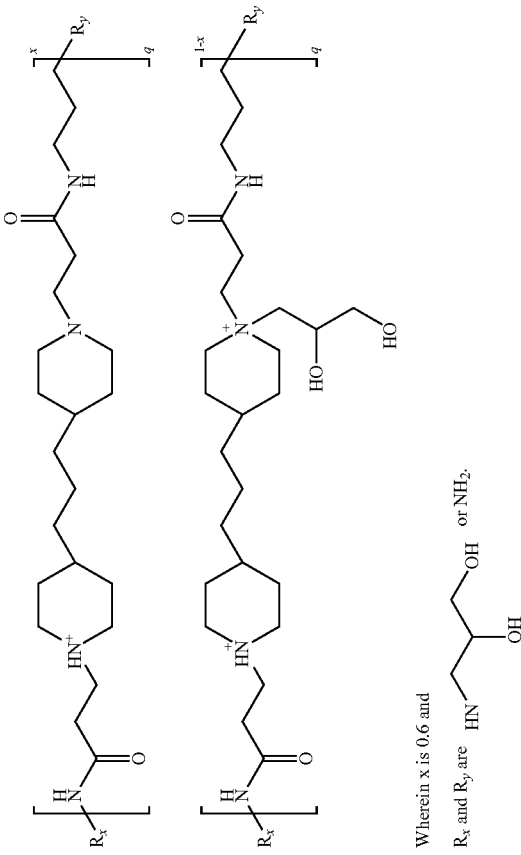 Wherein x is 0.6 and $R_x$ and $R_y$ are |

TABLE 1-continued
Amine Functional Polyamides
| Polymer Description | Structure |
|---|---|
| 40 mol % glycidol modified Poly(4,4-trimethylene dipiperidinebis-propanoic acid-diaminopropane) Mw 5000 | 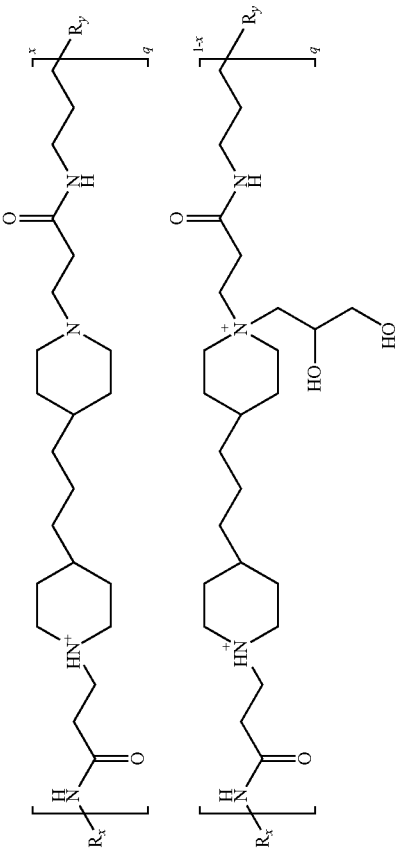 Wherein x is 0.6 and $R_x$ and $R_y$ are |
| 100 mol % glycidol modified Poly(4,4-trimethylene dipiperidinebis-propanoic acid-diaminopropane), Mw 8K | 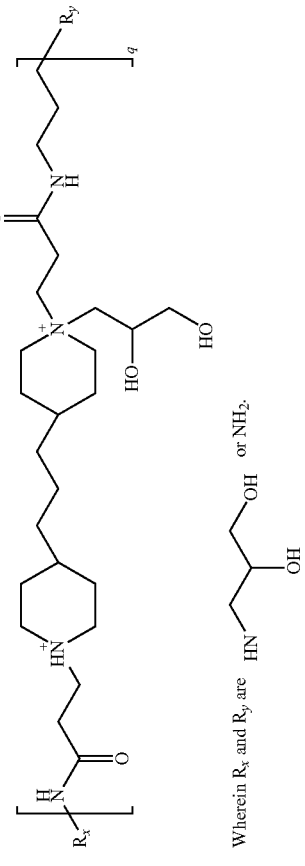 Wherein $R_x$ and $R_y$ are |

TABLE 1-continued

Amine Functional Polyamides

| Polymer Description | Structure |
|---|---|
| 25 mol % glycidol modified Poly(4,4-trimethylene dipiperidinebis-propanoic acid-diaminopropane), Mw 7800 | (structure shown) |

Wherein x is 0.75 and $R_x$ and $R_y$ are HN–CH$_2$–CH(OH)–CH$_2$OH or NH$_2$.

TABLE 1-continued

Amine Functional Polyamides

| Polymer Description | Structure |
|---|---|
| 50 mol % glycidol modified Poly(4,4-trimethylene dipiperidinebis-propanoic acid-diaminopropane), Mw 7800 | 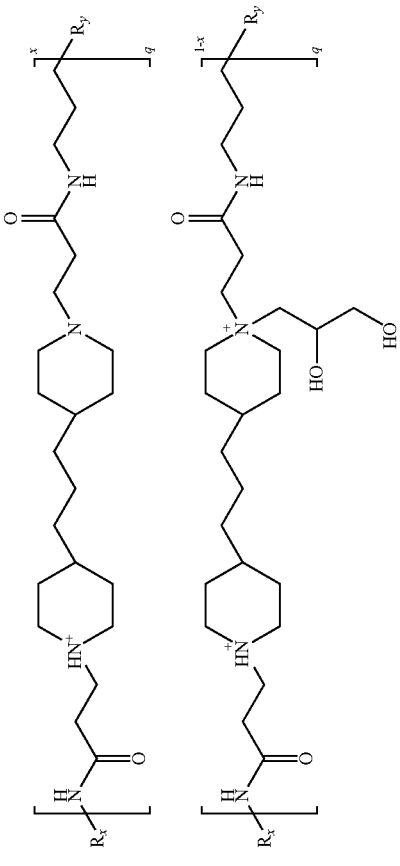 Wherein x is 0.5 and $R_x$ and $R_y$ are HN—CH$_2$—CH(OH)—CH$_2$—OH or NH$_2$ |
| 150 mol % glycidol modified Poly(4,4-trimethylene dipiperidinebis-propanoic acid-diaminopropane), Mw 7800 | 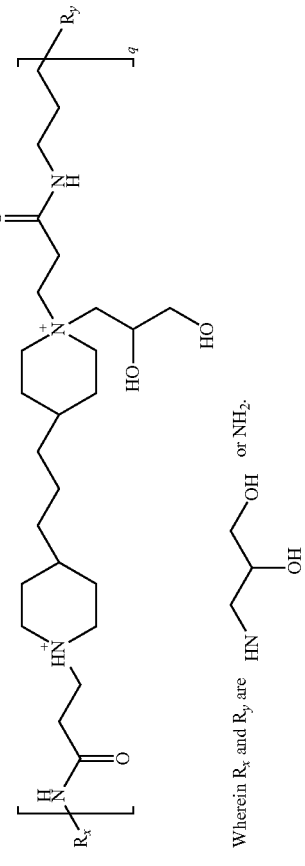 Wherein $R_x$ and $R_y$ are HN—CH$_2$—CH(OH)—CH$_2$—OH or NH$_2$ |

TABLE 1-continued

Amine Functional Polyamides

| Polymer Description | Structure |
|---|---|
| Poly(4,4'-trimethylene dipiperidinebis-propanoic acid-diaminopropane) modified with 200 mol % of glycidol, Mw 7800 | (structure shown) Wherein $R_x$ and $R_y$ are $\mathrm{HN}\!\!-\!\!\mathrm{CH_2CH(OH)CH_2OH}$, $\mathrm{OH}$ or $\mathrm{NH_2}$ |
| Poly (4,4'-trimethylene dipiperidine bispropanoic acid-3-(dimethylamino) 1-propylamine), Mw 1K | (structure shown) |
| Poly(2,2'-bipyrrolidine bispropanoic acid-diaminopropane), Mw 2.5K | (structure shown) |

TABLE 1-continued
Amine Functional Polyamides
| Polymer Description | Structure |
|---|---|
| Poly(2,2'-bipyrrolidine bispropanoic acid-butyl-diamine) | 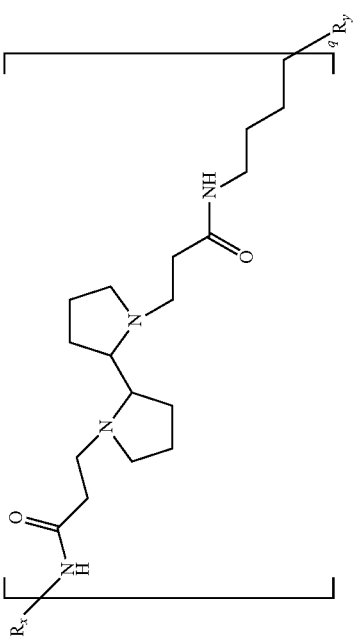 |
| Poly(2,2'-bipyrrolidine bispropanoic acid-penta-diamine) | 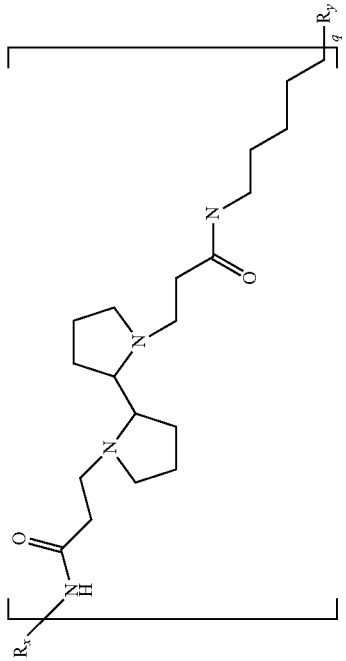 |

TABLE 1-continued

Amine Functional Polyamides

| Polymer Description | Structure |
|---|---|
| Poly(2,2'-bipyrrolidine bispropanoic acid-ethyl-diamine) | 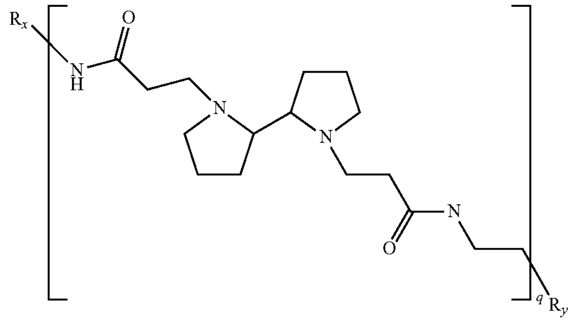 |
| Poly(4,4-trimethylene dipiperidinebis-propanoic acid-aminomethyl-benzene) | 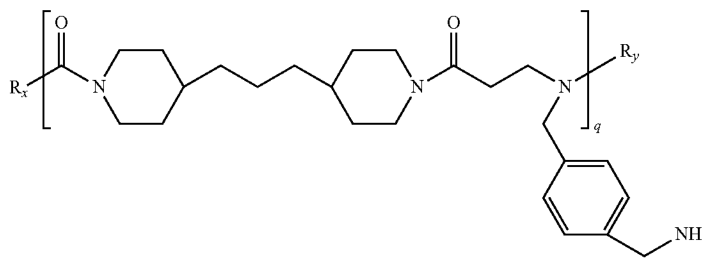 |
| Poly[4,4-trimethylene dipiperidinebis-propanoic acid-(1-aminomethyl-4-guanidinemethyl-benzene)] | 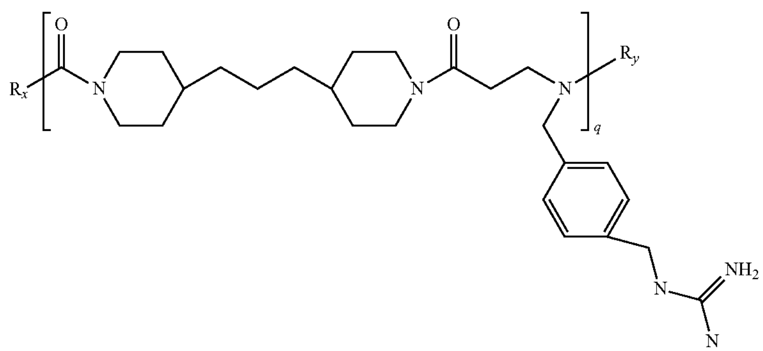 |

TABLE 1-continued

Amine Functional Polyamides

| Polymer Description | Structure |
|---|---|
| Carboxy terminated Poly(4,4-trimethylene dipiperidinebis-propanoic acid-diaminopropane) | 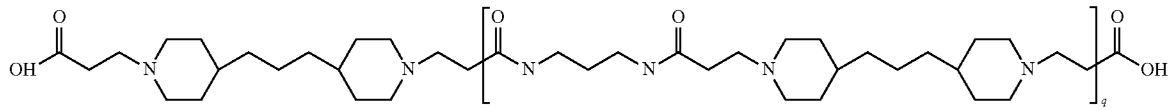 |
| Methyl ester terminated Poly(4,4-trimethylene dipiperidinebis-propanoic acid-diaminopropane) | 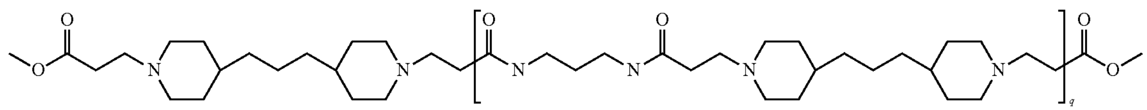 |
| Guanidine terminated Poly(4,4-trimethylene dipiperidinebis-propanoic acid-diaminopropane) | 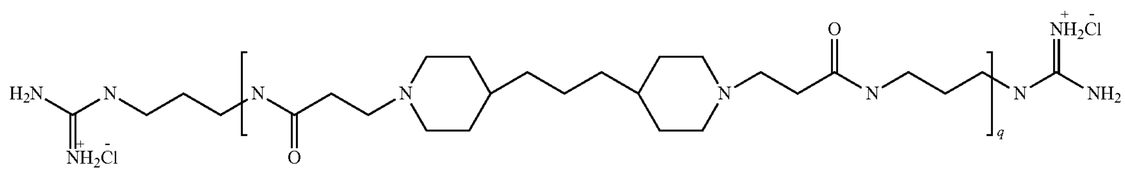 |
| Guanidine terminated Poly(4,4-trimethylene dipiperidinebis-propanoic acid-diaminopropane) Mw 4700 | 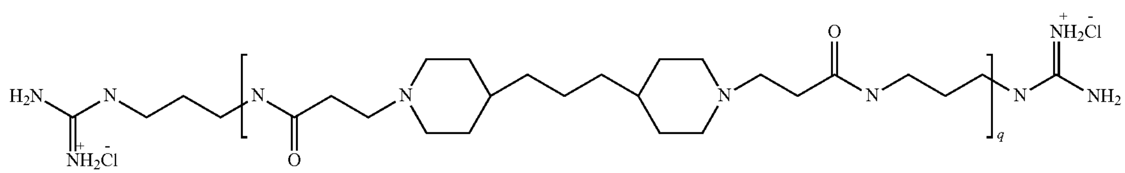 |
| Guanidine terminated poly(4,4-trimethylene dipiperidinebis-propanoic acid-diaminopropane) Mw 7700 | 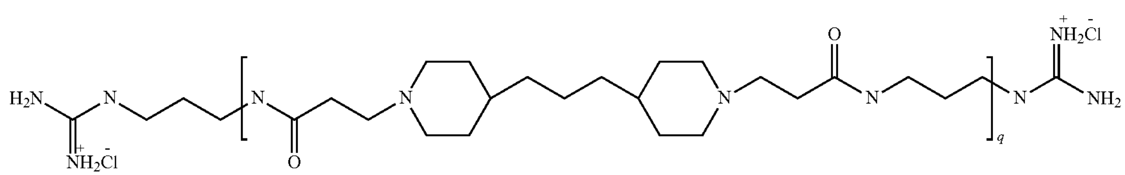 |

TABLE 1-continued

Amine Functional Polyamides

| Polymer Description | Structure |
|---|---|
| Poly(4,4-trimethylene dipiperidinebis-propanoic acid-diaminopropane) (guanidine ended) | 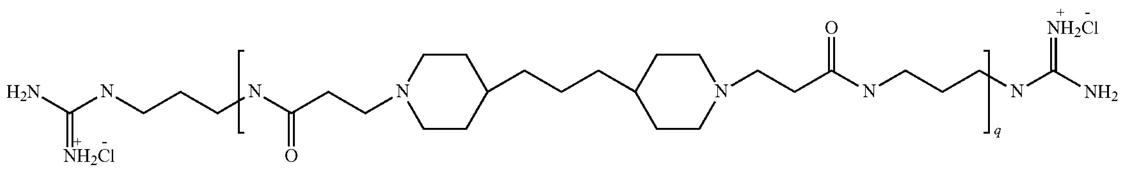 |
| 4,4-trimethylene dipiperidinebis-propanoic acid-diaminopropane | 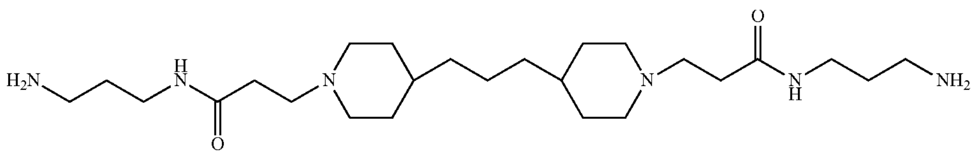 [SMILES: NCCCNC(=O)CCN1CCC(CCCC2CCN(CCC(=O)NCCCN)CC2)CC1] |
| 4-guanidinobenzene terminated Poly(4,4-trimethylene dipiperidinebis-propanoic acid-diaminopropane) | 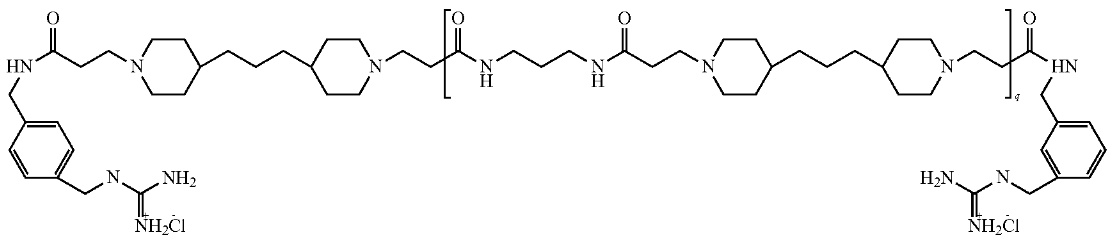 |
| Poly(4,4-trimethylenedi-piperidine bisethylacrylamide-co-1,3-diamine propane) | |

TABLE 1-continued

Amine Functional Polyamides

| Polymer Description | Structure |
|---|---|
| Poly(4,4-trimethylenedipiperidine bisethylacrylamide-co-1-amino-3-guanidine propane) | |
| 4,4-trimethylene dipiperidinebis-propanoic acid-1-amino-3-guanidine propane | |
| Poly(4,4-trimethylenedipiperidine bisethylacrylamide-1,3-diamine propane)-co-Poly(4,4-trimethylenedipiperidine bisethylacrylamide-1-aminobutyl-3-carbamoyl-pyridinium) | |

TABLE 1-continued
Amine Functional Polyamides
| Polymer Description | Structure |
|---|---|
| Poly(4,4'-trimethylenedipiperidine bisethylacrylamine-1-aminobutyl-3-carbamoyl-pyridinium) | 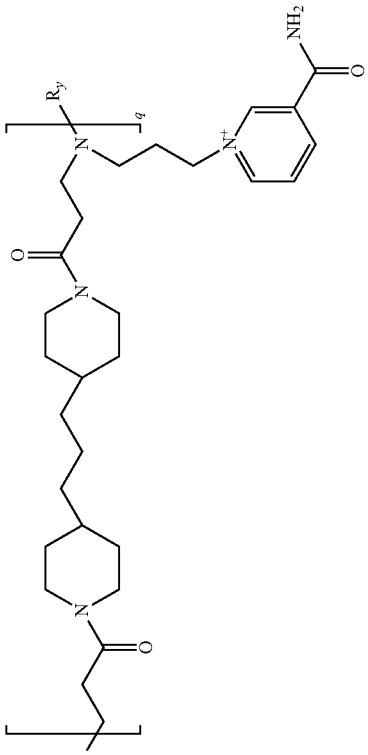 |
| 4,4'-trimethylene dipiperidinebis-propanoic acid-diaminopropane pentamer | 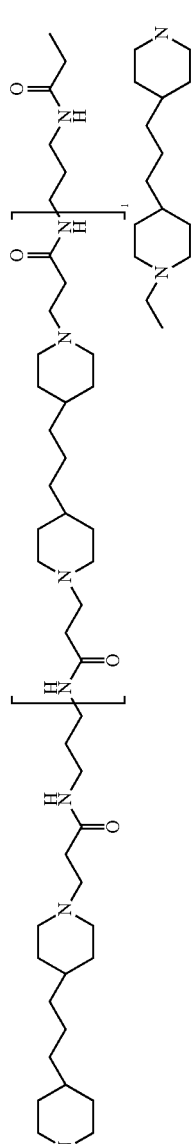 |
| 4,4'-trimethylene dipiperidinebis-propanoic acid-diaminopropane heptamer | 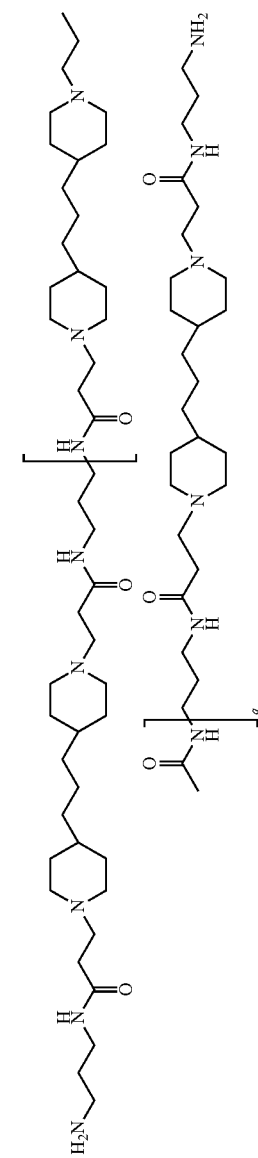 |

TABLE 1-continued
Amine Functional Polyamides
| Polymer Description | Structure |
|---|---|
| Poly(4,4'-trimethylene dipiperidinebis-propanoic acid-N-glycidol dipropylene triamine) | 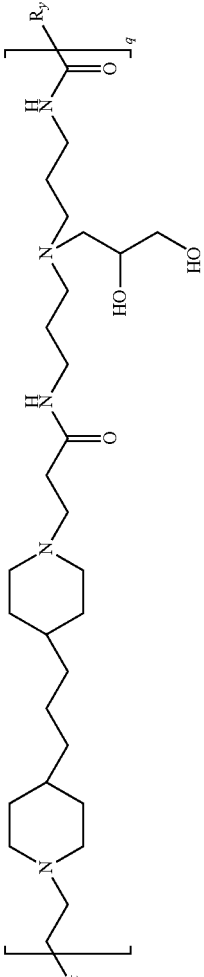 |
| Poly(4,4'-trimethylene dipiperidinebis-propanoic acid-N-glycidol diethylene triamine) | 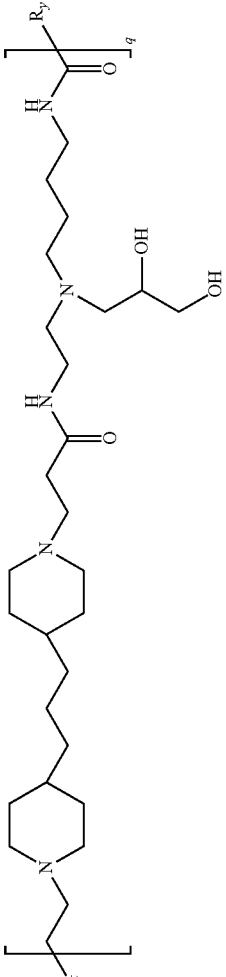 |
| Poly(4,4'-trimethylene dipiperidinebis-propanoic acid-N-glycidol diethylene triamine) | 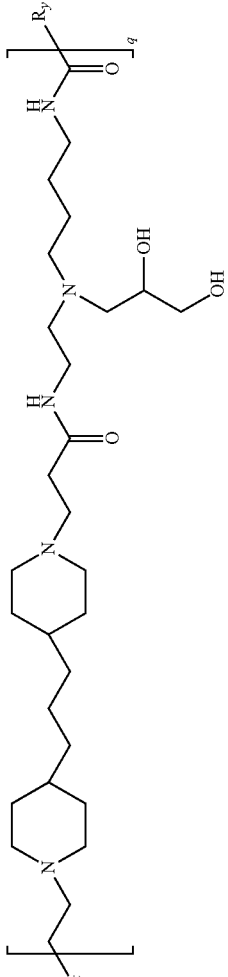 |

In an embodiment of the invention, the amine functional polyamides are administered as a pharmaceutical composition. In another embodiment of the invention, the amine functional polyamides are administered in an effective amount to achieve the desired therapeutic effect. The skilled artisan will be able to determine the effective amount of the amine functional polyamides depending on the individual and the condition being treated.

In one embodiment of the invention, the amine functional polyamides are used in the treatment all forms of mucositis, and are particularly effective when used to treat oral mucositis. Treatment includes prophylactic and therapeutic uses of the disclosed amine functional polyamides and uses of the disclosed pharmaceutical compositions comprising amine functional polyamides. Desired prophylactic effects include prevention and inhibition of mucositis, reduction in severity of mucositis, reduction in size of mucositis lesions and reduction in likelihood of developing mucositis through the application or administration of amine functional polyamides or pharmaceutical compositions comprising amine functional polyamides. Desired therapeutic effects include amelioration of the discomfort associated with the mucositis, and/or increased rate of healing of mucositis lesion.

In one embodiment, the amine functional polyamides and pharmaceutical compositions comprising amine functional polyamides can be used to treat all forms of infection, including but not limited to SSI, lung infection in CF patients, and *C. aeruginosa* lung infection in CF patients with or without biofilm formation. The amine functional polyamides and pharmaceutical compositions comprising amine functional polyamides can be used in prophylactic and therapeutic applications to treat and prevent infection.

In another embodiment, the amine functional polyamides and pharmaceutical compositions comprising amine functional polyamides can be used to treat all forms of SSIs. Treatment includes prophylactic and therapeutic uses of the disclosed amine functional polyamides and uses of the disclosed pharmaceutical compositions comprising amine functional polyamides. A desired prophylactic use is the immediate administration of amine functional polyamides or pharmaceutical compositions comprising amine functional polyamides to the surgical wound post-surgery in order to prevent and/or reduce the likelihood of developing a SSI. Another desired prophylactic use is the administration of amine functional polyamides or pharmaceutical compositions comprising amine functional polyamides prior to surgery in order to prevent and/or reduce the likelihood of developing a SSI. Desired therapeutic effects include the treatment of an existing SSI through the application or administration of amine functional polyamides or pharmaceutical compositions comprising an amine functional polyamide.

In another embodiment, the amine functional polyamides and pharmaceutical compositions comprising amine functional polyamides can be used to treat all forms of lung infections and chronic lung infections associated with CF, including *C. aeruginosa* lung infections in CF patients with or without biofilm formation. Treatment includes prophylactic and therapeutic uses of the disclosed amine functional polyamides and uses of the disclosed pharmaceutical compositions comprising amine functional polyamides. Desired therapeutic effects include the treatment of an existing lung infection or chronic lung infection through the administration of amine functional polyamides or pharmaceutical compositions comprising an amine functional polyamide. In one embodiment, the amine functional polyamides and pharmaceutical compositions comprising amine functional polyamides are used to treat *P. aeruginosa* infections associated with CF without biofilm formation. In another embodiment, the amine functional polyamides and pharmaceutical compositions comprising amine functional polyamides are used to treat *P. aeruginosa* infections associated with CF with biofilm formation. A desired prophylactic use is the administration of amine functional polyamides or pharmaceutical compositions comprising amine functional polyamides to the CF patient in order to prevent and/or reduce the likelihood of developing a lung infection, including *C. aeruginosa* lung infections. Desired therapeutic effects include the treatment of an existing lung infection or chronic lung infection through the administration of amine functional polyamides or pharmaceutical compositions comprising an amine functional polyamide.

The amine functional polyamides of the present invention may be administered alone or in a pharmaceutical composition comprising amine functional polyamides. Suitable pharmaceutical compositions may comprise an amine functional polyamide and one or more pharmaceutically acceptable excipients. The form in which the polymers are administered, for example, powder, tablet, capsule, solution, or emulsion, depends in part on the route by which it is administered. The amine functional polyamides can be administered, for example, topically, orally, intranasally, by aerosol or rectally. Suitable excipients include, but are not limited to, are inorganic or organic materials such as gelatin, albumin, lactose, starch, stabilizers, melting agents, emulsifying agents, salts and buffers. Suitable pharmaceutically acceptable excipients for topical formulations such as ointments, creams and gels include, but are not limited to, commercially available inert gels or liquids supplemented with albumin, methyl cellulose, or a collagen matrix.

The amine functional polyamides and pharmaceutical compositions comprising amine functional polyamides can be administered alone or in combination with one or more additional drugs. Additional drugs administered in combination with the amine functional polyamides and pharmaceutical compositions comprising amine functional polyamides of the present invention include antibiotics and other compounds, including those used prophylactically and/or therapeutically for the treatment or prevention of mucositis and infection, including SSI and lung infection and chronic lung infection associated with CF, especially *P. aeruginosa* infection, with or without biofilm formation. The additional drugs may be administered concomitantly with the amine functional polyamide or pharmaceutical compositions comprising amine functional polyamides. The additional drugs may also be administered in series with the amine functional polyamide or pharmaceutical compositions comprising amine functional polyamides. The pharmaceutical composition comprising amine functional polyamides may also further comprise a drug used prophylactically and/or therapeutically for the treatment or prevention of mucositis and infection, including SSI and lung infection and chronic lung infection associated with CF, especially *P. aeruginosa* infection, with or without biofilm formation.

EXAMPLES

Example 1

In vitro Studies

Example 1-1

Cytotoxicity Assay, RPTEC Cells and NHDF Cells

Mammalian cell cytotoxicity assays were performed using two primary human cell lines: renal proximal tubule epithelial cells (RPTEC—Cambrex CC-2553) and normal human dermal fibroblasts (NHDF—Cambrex CC-2509). Cells were plated at 3,000 cells/well (RPTEC) or 5,000 cells/well (NHDF) in 96-well plates and incubated overnight at 37° C.

The compounds were added to the wells, and the cells were incubated for 4 days. Alomar Blue was added to one set of plates and incubated for 4 hours. The plates were read when the compound was added (time zero) and at the end of the study. Fluorescence was read using 530 nm (excitation) and 590 nm (emission) according to the manufacturer's instructions. The 50% inhibitory concentration ($IC_{50}$) was calculated as 50% of the maximum signal minus the value at time zero. The 50% lethal concentration ($LC_{50}$) was calculated as 50% of the time zero value minus the minimum signal.

Table 2 displays the renal proximal tubule epithelial cells and normal human dermal fibroblasts $IC_{50}$ and $LC_{50}$ for selected compounds.

Example 1-2

Cytotoxicity Assay, Human Lung Epithelial Cells

Cytoxicity of the polymers towards human lung epithelial cells was performed using human lung epithelial Carcinoma cell line (A 549—ATCC # CCL-185). The cells were incubated for 96 hours at 7° C. with 5% $CO_2$ in a 96-well plate. CellTiter-Glo® (Promega) reagent was added to the plates. The plates were read by measuring the luminescence arising from luciferase catalyzed reaction of luciferin with ATP according to the manufacturer's suggested protocol. The concentration of ATP is directly proportional to cell viability; accordingly, higher luminescence measures high cell viability.

Table 2 displays the human lung epithelial cells $IC_{50}$ for selected compounds.

Example 1-3

Erythrocyte Lysis Assay

The compounds were incubated overnight at 37° C. in Dulbecco's phosphate-buffered saline containing fresh washed erythrocytes at a hematocrit of 1%. After incubation, the plates were centrifuged and the supernatant transferred to flat-bottomed 96-well plates. The supernatant was assayed using the QuantiChrom Hemoglobin kit according to the manufacturer's instructions. The $IC_{50}$ values were calculated using GraphPad Prism.

Table 2 displays the $IC_{50}$ values for selected compounds.

Example 1-4

Minimum Inhibitory Concentration Assay

The minimum inhibitory concentration (MIC) assay determines the lowest concentration of an antimicrobial agent required to inhibit the growth of test organisms after incubation. MIC assays were performed against an internal standard panel of organisms to identify compounds with antimicrobial activity. The MIC assay was subsequently repeated against other specialized microbial panels. Assays were conducted against the following clinically relevant microorganisms: *Staphylococcus aureus* subsp. *aureus*, *Staphylococcus epidermis*, *Escherichia coli*, *Pseudomonas aeruginosa*, *Haemophilius influenzae*. The compounds were tested for bacteriocidal activity, time course of killing, toxicity against tissue culture cells grown in vitro, and in some cases were tested for antimicrobial activity in vivo.

The MIC assays were performed according to the Performance Standards for Antimicrobial Susceptibility Testing, 2006, vol. M100-S15, Fifteenth Informational Supplement, NCCLS, 940 West Valley Road, Suite 1400, Wayne, Pa. 19087.

The polymers tested were dissolved in 0.85% saline to a final concentration of either 830 or 1000 μg/mL and the pH was adjusted to 7.0. The solution was then filter-sterilized through a 0.22 μm filter. Two-fold serial dilutions of polymer were prepared in Mueller-Hinton broth with cations aliquotted into 96-well microtiter plates. The plates were then inoculated with $5 \times 10^5$ cells/mL of target organism and incubated 18-24 hours at 35° C. The optical density (OD) was read at 590 nm, and microorganism growth was scored (OD>0.1 is considered to be growth; OD<0.1 is considered to be growth inhibition). The MIC value is the lowest concentration of compound that inhibits growth; accordingly, a higher MIC value indicates less potency where a lower MIC valued indicated more potency.

MIC values of representative amine functional polyamides against clinically relevant microorganisms are presented in Table 2.

TABLE 2

In vitro Results of Representative Amine Functional Polyamides
Cytotoxicity Assay [Kidney Epithelial and Human Dermal Fibroblast $IC_{50}$ and $LC_{50}$],
Erythrocyte Lysis Assay [Hemolysis $IC_{50}$],
and MIC values against Clinically Relevant Microorganisms

| Polymer Description | Cytotoxicity (Kidney Epithelial $IC_{50}$) | Cytotoxicity (Kidney Epithelial $LC_{50}$) | Cytotoxicity (Human Dermal Fibroblast $IC_{50}$) | Cytotoxicity (Human Dermal Fibroblast $LC_{50}$) | Lung Epi $IC_{50}$ | Erythrocyte Lysis (Hemolysis $IC_{50}$) | Staphylococcus aureus subsp. aureus (MIC) | Staphylococcus epidermis (MIC) | Escherichia coli (MIC) | Pseudomonas aeruginosa (MIC) | Haemophilus influenzae (MIC) |
|---|---|---|---|---|---|---|---|---|---|---|---|
| Poly(4,4-trimethylene dipiperidine-bispropanoic acid-diamino-propane) <10K | 32.2 | 55.7 | 141.3 | 189.3 | 391 | >6400 | 1.0 | 0.3 | 2.0 | 32 | 16.0 |
| Poly(4,4-trimethylene dipiperidine-bispropanoic acid-diamino-butane) >10K | 5.3 | 8.7 | 16.3 | 22.1 | 74.1 | >6400 | 4.0 | 1.0 | 4.0 | 32.0 | 16.0 |

TABLE 2-continued

In vitro Results of Representative Amine Functional Polyamides
Cytotoxicity Assay [Kidney Epithelial and Human Dermal Fibroblast $IC_{50}$ and $LC_{50}$],
Erythrocyte Lysis Assay [Hemolysis $IC_{50}$],
and MIC values against Clinically Relevant Microorganisms

| Polymer Description | Cytotoxicity (Kidney Epithelial $IC_{50}$) | Cytotoxicity (Kidney Epithelial $LC_{50}$) | Cytotoxicity (Human Dermal Fibroblast $IC_{50}$) | Cytotoxicity (Human Dermal Fibroblast $LC_{50}$) | Lung Epi $IC_{50}$ | Erythrocyte Lysis (Hemolysis $IC_{50}$) | Staphylococcus aureus subsp. aureus (MIC) | Staphylococcus epidermis (MIC) | Escherichia coli (MIC) | Pseudomonas aeruginosa (MIC) | Haemophilus influenzae (MIC) |
|---|---|---|---|---|---|---|---|---|---|---|---|
| Poly(4,4-trimethylene dipiperidine-bispropanoic acid-diaminobutane) <10K | 28.6 | 61.9 | 138.3 | 196.2 | 377.9 | >6400 | 4.0 | 1.0 | 4.0 | 128.0 | 16.0 |
| Poly(4,4-trimethylene dipiperidine-bispropanoic acid-diaminoethane) <10K | 33 | 78 | 178 | 273 | 799 | >6400 | 32.0 | 4.0 | 16.0 | 128.0 | 128.0 |
| Poly(4,4-trimethylene dipiperidine-bispropanoic acid-diaminotri-PEG) <10K | 45.6 | 133.3 | 218.4 | 436.5 | 427.1 | 2066 | 128.0 | 128.0 | 32.0 | 128.0 | 128.0 |
| Poly(4,4-trimethylene dipiperidine-bispropanoic acid-diaminotri-PEG) >10K | 2.7 | 6.9 | 8.5 | 18.8 | 29.0 | 1792 | 128.0 | 8.0 | 8.0 | 64.0 | 128.0 |
| Poly(4,4-trimethylene dipiperidine-bispropanoic acid-diaminopropane) <10K | 32.2 | 55.7 | 141.3 | 189.3 | — | >6400 | 1.0 | 0.5 | 4.0 | 64.0 | 16.0 |
| Poly(4,4-trimethylene dipiperidine-bispropanoic acid-N(2-aminoethyl)-diaminoethane) | <1.463 | <1.463 | 1.7 | 2.0 | 6.5 | 9 | 4.0 | 0.5 | 8.0 | 16.0 | 64.0 |
| Poly(4,4'-trimethylene dipiperidine-bispropanoic acid-N(3-aminopropyl) 1,3-propane diamine) <10K | <1.463 | <1.463 | <1.463 | <1.463 | 13.9 | 2220.0 | 1.0 | 0.5 | 8.0 | 64.0 | 32.0 |
| Poly(4,4-trimethylene dipiperidine-bispropanoic acid-diaminopropane) <10K | 10.8 | 25.6 | 62.6 | 99.7 | 333.0 | >6400 | 1.0 | 0.5 | 4.0 | 16.0 | 16.0 |
| Poly(4,4'-trimethylene dipiperidine-bispropanoic acid-3,3'-diamino-N-methyl-dipropylamine) <10K | <1.463 | <1.463 | <1.463 | 1.9 | 65.0 | >6400 | 8.0 | 1.0 | 16.0 | 64.0 | 64.0 |

TABLE 2-continued

In vitro Results of Representative Amine Functional Polyamides
Cytotoxicity Assay [Kidney Epithelial and Human Dermal Fibroblast $IC_{50}$ and $LC_{50}$],
Erythrocyte Lysis Assay [Hemolysis $IC_{50}$],
and MIC values against Clinically Relevant Microorganisms

| Polymer Description | Cytotoxicity (Kidney Epithelial $IC_{50}$) | Cytotoxicity (Kidney Epithelial $LC_{50}$) | Cytotoxicity (Human Dermal Fibroblast $IC_{50}$) | Cytotoxicity (Human Dermal Fibroblast $LC_{50}$) | Lung Epi $IC_{50}$ | Erythrocyte Lysis (Hemolysis $IC_{50}$) | Staphylococcus aureus subsp. aureus (MIC) | Staphylococcus epidermis (MIC) | Escherichia coli (MIC) | Pseudomonas aeruginosa (MIC) | Haemophilus influenzae (MIC) |
|---|---|---|---|---|---|---|---|---|---|---|---|
| Poly(4,4'-trimethylene dipiperidine-bispropanoic acid-2,2'-diamino-N-methyl-diethylamine) | 2.9 | 7.2 | 9.3 | 20.1 | 125.5 | >6400 | 4.0 | 1.0 | 8.0 | 64.0 | 64.0 |
| Poly(4,4'-trimethylene dipiperidine-bispropanoic acid-1,4-benzyldiamine) <10K | 2.0 | 2.9 | 4.703 | 5.1 | 31.3 | 87.0 | 32.0 | 8.0 | 16.0 | 128.0 | 128.0 |
| Poly(piperazine-bispropanoic acid-1,2-bis(2-aminoethoxy)ethane) <10K | >3200 | >3200 | >3200 | >3200 | >6400 | >6400 | 128.0 | 128.0 | 128.0 | 128.0 | 128.0 |
| Poly(piperazine-bispropanoic acid-2,2-diaminodiethylamine) <10K | 212.1 | 838.5 | 1111.6 | 1999.8 | >6400 | >6400 | 128.0 | 64.0 | 128.0 | 128.0 | 128.0 |
| Poly(piperazine-bispropanoic acid-3,3'-diamino-N-methyl-dipropylamine) <10K | 5.3 | 33.7 | 94.7 | 246.2 | 4164.4 | >6400 | 128.0 | 32.0 | 128.0 | 128.0 | 128.0 |
| Poly(piperazine-bispropanoic acid-N(3-aminopropyl)1,3-propane diamine) <10K | <1.463 | 3.0 | 15.3 | 35.0 | 497.0 | >6400 | 8.0 | 4.0 | 128.0 | 128.0 | 128.0 |
| Poly(piperazine-bispropanoic acid-N-methyl-2,2-diaminodiethylamine) <10K | 1204.2 | >3200 | 3068.6 | >3200 | >6400 | >6400 | 128.0 | 128.0 | 128.0 | 128.0 | 128.0 |
| Poly(4,4'-trimethylene-dipiperidinebispropanoic acid-2,2'-diamino-diethylamine) 5.5K | <1.463 | 1.5 | 2.0 | 3.4 | 14.6 | 88.0 | 4.0 | 0.3 | 4.0 | 16.0 | 64.0 |
| Poly(4,4'-dipiperidine-bispropanoic acid-2,2'-diamino-diethylamine) 5.1K | <1.5 | 2 | 2 | 4 | 50.0 | 1284.0 | 1.0 | 0.5 | 16.0 | 64.0 | 128.0 |
| Poly(4,4'-dipiperidine-bispropanoic acid-2,2'-diamino N-methyl diethylamine) <5K | <1.5 | 2 | 4 | 7 | 93.0 | >6400 | 2.0 | 0.5 | 32.0 | 64.0 | 128.0 |

TABLE 2-continued

In vitro Results of Representative Amine Functional Polyamides
Cytotoxicity Assay [Kidney Epithelial and Human Dermal Fibroblast IC$_{50}$ and LC$_{50}$],
Erythrocyte Lysis Assay [Hemolysis IC$_{50}$],
and MIC values against Clinically Relevant Microorganisms

| Polymer Description | Cytotoxicity (Kidney Epithelial IC$_{50}$) | Cytotoxicity (Kidney Epithelial LC$_{50}$) | Cytotoxicity (Human Dermal Fibroblast IC$_{50}$) | Cytotoxicity (Human Dermal Fibroblast LC$_{50}$) | Lung Epi IC$_{50}$ | Erythrocyte Lysis (Hemolysis IC$_{50}$) | Staphylococcus aureus subsp. aureus (MIC) | Staphylococcus epidermis (MIC) | Escherichia coli (MIC) | Pseudomonas aeruginosa (MIC) | Haemophilus influenzae (MIC) |
|---|---|---|---|---|---|---|---|---|---|---|---|
| Poly(4,4'-dipiperidine-bispropanoic acid-2,2'-diamino N-methyl diethylamine) <5K | 5 | 9 | 20 | 30 | 294.0 | >6400 | 8.0 | 0.5 | 32.0 | 32.0 | 128.0 |
| Poly(4,4'-dipiperidine-bispropanoic acid-2,2'-diamino N-methyl diethylamine) ~5K | 11 | 21 | 61 | 88 | 823.0 | >6400 | 8.0 | 1.0 | 64.0 | 64.0 | 128.0 |
| Poly(4,4'-dipiperidine-bispropanoic acid-3,3'-diamino-dipropylamine) <5K | <1.5 | <1.5 | <1.5 | <1.5 | 10.0 | 300.0 | 1.0 | 0.3 | 16.0 | 32.0 | 128.0 |
| Poly(4,4'-dipiperidine-bispropanoic acid-3,3'-diamino-dipropylamine) ~5K | <1.5 | <1.5 | 2 | 3 | 30.0 | >6400 | 1.0 | 0.5 | 16.0 | 64.0 | 128.0 |
| Poly(4,4'-dipiperidine-bispropanoic acid-3,3'-diamino-N-methyl-dipropylamine) ~5K | <1.5 | 2 | 3 | 5 | 81.0 | >6400 | 8.0 | 1.0 | 32.0 | 64.0 | 128.0 |
| Poly(4,4'-dipiperidine-bispropanoic acid-3,3'-diamino-N-methyl-dipropylamine) >5K | <1.5 | <1.5 | 2 | 3 | 26.0 | 3622.0 | 2.0 | 0.5 | 16.0 | 32.0 | 128.0 |
| Poly(4,4'-trimethylene-dipiperidinebis-propanoic acid-2,2'-diamino diethylamine) ~14,000 | <1.463 | <1.463 | 2.1 | 2.8 | 6.8 | 9.0 | 4.0 | 1.0 | 8.0 | 16.0 | 128.0 |
| Poly(piperazine-bispropanoic acid-1,3-diamino-propane) ~3,700 | 924 | >3200 | >3200 | >3200 | >6400 | >6400 | 128.0 | 128.0 | 128.0 | 128.0 | 128.0 |
| Poly(piperazine-bispropanoic acid-1,4-diaminobutane) ~4,400 | 541 | 1946 | 1905 | 3080 | 4539.0 | 3388.0 | 128.0 | 64.0 | 128.0 | 128.0 | 128.0 |

TABLE 2-continued

In vitro Results of Representative Amine Functional Polyamides
Cytotoxicity Assay [Kidney Epithelial and Human Dermal Fibroblast $IC_{50}$ and $LC_{50}$],
Erythrocyte Lysis Assay [Hemolysis $IC_{50}$],
and MIC values against Clinically Relevant Microorganisms

| Polymer Description | Cytotoxicity (Kidney Epithelial $IC_{50}$) | Cytotoxicity (Kidney Epithelial $LC_{50}$) | Cytotoxicity (Human Dermal Fibroblast $IC_{50}$) | Cytotoxicity (Human Dermal Fibroblast $LC_{50}$) | Lung Epi $IC_{50}$ | Erythrocyte Lysis (Hemolysis $IC_{50}$) | Staphylococcus aureus subsp. aureus (MIC) | Staphylococcus epidermis (MIC) | Escherichia coli (MIC) | Pseudomonas aeruginosa (MIC) | Haemophilus influenzae (MIC) |
|---|---|---|---|---|---|---|---|---|---|---|---|
| Poly(4,4'-dipiperidine-bispropionic acid-1,3-diaminopropane) <5K | 6 | 11 | 7 | 16 | 22.0 | >6400 | 1.0 | 0.1 | 16.0 | 1.0 | 32.0 |
| Poly(4,4'-dipiperidine-bispropionic acid-1,4-diaminobutane) <5K | 4 | 7 | 5 | 17 | 22.0 | >6400 | 2.0 | 0.3 | 8.0 | 8.0 | 32.0 |
| Poly(4,4'-dipiperidine-bispropionic acid-ethylenediamine) <5K | 8 | 21 | 19 | 29 | 77.0 | >6400 | 4.0 | 0.5 | 16.0 | 32.0 | 128.0 |
| Poly(4,4'-trimethylene-dipiperidine-1,3-diamnino-propane-N,N'-di-3-propionic acid) <5K | 2 | 3 | 2 | 3 | 4.0 | 6.3 | 16.0 | 4.0 | 8.0 | 16.0 | 128.0 |
| Poly(4,4'-trimethylene-dipiperidinebis-propionic acid 2-dydroxy 1,3-diamino-propane) <5K | 15 | 80 | 50 | 127 | 63.0 | >6400 | 4.0 | 1.0 | 8.0 | 128.0 | 32.0 |
| Poly(4,4'-trimethylene-dipiperidinebis-propionic acid-bis(4-amino-butyl)ether) <5K | 2 | 5 | 3 | 5 | 8.0 | 165.0 | 128.0 | 8.0 | 8.0 | 128.0 | 16.0 |
| Poly (4,4'-trimethylene dipiperidine bispropanoic acid-4,4'-trimethylene dipiperidine) | <1.463 | 3 | 3 | 4 | 2 | 5.6 | 16.0 | 4.0 | 16.0 | 32.0 | 128.0 |
| Poly (4,4'-trimethylene dipiperidine bispropanoic acid--N,N'-dimethyl-1,3-diamino-propane) | <1.463 | 2 | 5 | 11 | 6 | 11.3 | 128.0 | 4.0 | 4.0 | 16.0 | 128.0 |
| Poly (4,4'-trimethylene dipiperidine bispropanoic acid-piperazine) | 12 | 22 | 53 | 75 | 21 | 59.0 | 128.0 | 128.0 | 128.0 | 128.0 | 128.0 |

TABLE 2-continued

In vitro Results of Representative Amine Functional Polyamides
Cytotoxicity Assay [Kidney Epithelial and Human Dermal Fibroblast $IC_{50}$ and $LC_{50}$],
Erythrocyte Lysis Assay [Hemolysis $IC_{50}$],
and MIC values against Clinically Relevant Microorganisms

| Polymer Description | Cytotoxicity (Kidney Epithelial $IC_{50}$) | Cytotoxicity (Kidney Epithelial $LC_{50}$) | Cytotoxicity (Human Dermal Fibroblast $IC_{50}$) | Cytotoxicity (Human Dermal Fibroblast $LC_{50}$) | Lung Epi $IC_{50}$ | Erythrocyte Lysis (Hemolysis $IC_{50}$) | Staphylococcus aureus subsp. aureus (MIC) | Staphylococcus epidermis (MIC) | Escherichia coli (MIC) | Pseudomonas aeruginosa (MIC) | Haemophilus influenzae (MIC) |
|---|---|---|---|---|---|---|---|---|---|---|---|
| Poly(4,4-trimethylene dipiperidine-bispropanoic acid-diamino-propane) modified with 40 mol % of glycidol, 8K | 2 | 3 | 5 | 8 | 6.0 | 636.0 | 0.5 | 0.3 | 2.0 | 4.0 | 8.0 |
| Poly(4,4-trimethylene dipiperidine-bispropanoic acid-diamino-propane), 1650 | 3.1 | 5.5 | 9.4 | 15.5 | 21.5 | >3200 | 0.5 | 0.1 | 2.0 | 4.0 | 8.0 |
| Poly(4,4-trimethylene dipiperidine-bispropanoic acid-diamino-propane), 5K | 1.6 | 2.9 | 6.8 | 9.9 | 10.8 | 651.0 | 1.0 | 0.3 | 2.0 | 8.0 | 8.0 |
| Poly(4,4-trimethylene dipiperidine-bispropanoic acid-diamino-propane), 7.7K | <1.5 | <1.463 | 2.0 | 2.8 | 3.7 | 50.0 | 2.0 | 0.3 | 2.0 | 4.0 | 8.0 |
| Poly(4,4-trimethylene dipiperidine-bispropanoic acid-diamino-propane), 3K | 8.7 | 12.3 | 20.7 | 32.8 | 17 | 1260.0 | 1.0 | 0.3 | 4.0 | 16.0 | 4.0 |
| Poly(4,4-trimethylene dipiperidine-bispropanoic acid-diamino-propane) modified with 100 mol % of glycidol, 8K | 3.0 | 5.0 | 7.0 | 11.0 | 7.0 | 500.0 | 8.0 | 0.5 | 8.0 | 16.0 | 16.0 |
| Poly(4,4-trimethylene dipiperidine-bispropanoic acid-4,4'-dipiperidine), 10,631 | <1.5 | 2.0 | 2.0 | 4 | <1.5 | 3.2 | 16.0 | 4.0 | 8.0 | 16.0 | 128.0 |
| Poly(4,4-trimethylene dipiperidine-bispropanoic acid-histamine), 2.3K | 7.0 | 16.0 | 18.0 | 27.0 | 9.0 | 19.0 | 128.0 | 32.0 | 32.0 | 128.0 | 128.0 |

TABLE 2-continued

In vitro Results of Representative Amine Functional Polyamides
Cytotoxicity Assay [Kidney Epithelial and Human Dermal Fibroblast IC$_{50}$ and LC$_{50}$],
Erythrocyte Lysis Assay [Hemolysis IC$_{50}$],
and MIC values against Clinically Relevant Microorganisms

| Polymer Description | Cytotoxicity (Kidney Epithelial IC$_{50}$) | Cytotoxicity (Kidney Epithelial LC$_{50}$) | Cytotoxicity (Human Dermal Fibroblast IC$_{50}$) | Cytotoxicity (Human Dermal Fibroblast LC$_{50}$) | Lung Epi IC$_{50}$ | Erythrocyte Lysis (Hemolysis IC$_{50}$) | Staphylococcus aureus subsp. aureus (MIC) | Staphylococcus epidermis (MIC) | Escherichia coli (MIC) | Pseudomonas aeruginosa (MIC) | Haemophilus influenzae (MIC) |
|---|---|---|---|---|---|---|---|---|---|---|---|
| Poly(4,4-trimethylene dipiperidine-bispropanoic acid-diamino-propane), 3250 | 5.8 | 10.3 | — | — | — | >3200 | 0.5 | 0.1 | 2.0 | 8.0 | 8.0 |
| Poly(4,4-trimethylene dipiperidine-bispropanoic acid-diamino-propane), 4700 | 1.9 | 3.3 | — | — | — | 176.497 | 1.0 | 0.3 | 1.0 | 4.0 | 8.0 |
| Poly(4,4-trimethylene dipiperidine-bispropanoic acid-diamino-propane) modified with 200 mol % of glycidol, 7800 | 2 | 3 | — | — | — | 96.0 | 2.0 | 0.5 | 4.0 | 8.0 | 16.0 |
| Poly(4,4-trimethylene dipiperidine-bispropanoic acid-diamino-propane) modified with 150 mol % of glycidol, 7800 | 2 | 4 | — | — | — | 152.0 | 2.0 | 1.0 | 8.0 | 16.0 | 16.0 |
| Poly(4,4-trimethylene dipiperidine-bispropanoic acid-diamino propane) modified with 50 mol % of glycidol, 7800 | 2 | 4 | — | — | — | 110.0 | 4.0 | 0.5 | 8.0 | 16.0 | 16.0 |
| Poly(4,4-trimethylene dipiperidine-bispropanoic acid-diamino-propane), 2500 | 8.7 | 51.2 | — | — | — | >3200 | 0.5 | 0.3 | 8.0 | 64.0 | 32.0 |
| Poly(4,4-trimethylene dipiperidine-bispropanoic acid-diamino-propane) modified with 25 mol % of glycidol, 7800 | 2 | 2 | — | — | — | 55.0 | 2.0 | 0.5 | 4.0 | 8.0 | 16.0 |

TABLE 2-continued

In vitro Results of Representative Amine Functional Polyamides
Cytotoxicity Assay [Kidney Epithelial and Human Dermal Fibroblast IC$_{50}$ and LC$_{50}$],
Erythrocyte Lysis Assay [Hemolysis IC$_{50}$],
and MIC values against Clinically Relevant Microorganisms

| Polymer Description | Cytotoxicity (Kidney Epithelial IC$_{50}$) | Cytotoxicity (Kidney Epithelial LC$_{50}$) | Cytotoxicity (Human Dermal Fibroblast IC$_{50}$) | Cytotoxicity (Human Dermal Fibroblast LC$_{50}$) | Lung Epi IC$_{50}$ | Erythrocyte Lysis (Hemolysis IC$_{50}$) | Staphylococcus aureus subsp. aureus (MIC) | Staphylococcus epidermis (MIC) | Escherichia coli (MIC) | Pseudomonas aeruginosa (MIC) | Haemophilus influenzae (MIC) |
|---|---|---|---|---|---|---|---|---|---|---|---|
| Poly(4,4'-trimethylene dipiperidine-bispropanoic acid--3-(dimethylamino)1-propyl-amine), 1K | 32 | 70 | — | — | — | 182.0 | 128.0 | 32.0 | 128.0 | 128.0 | 128.0 |
| Poly(4,4'-trimethylene dipiperidine bispropanoic acid-N,N'-dimethyl-1,3-diamino-propane), 1K | 4 | 7 | — | — | — | 76.0 | 128.0 | 8.0 | 16.0 | 32.0 | 128.0 |
| Poly(2,2-bipyrrolidine bispropanoic acid-diamino-propane), 2.5K | 28 | 164 | — | — | — | >3200 | 128.0 | 16.0 | 128.0 | 128.0 | 128.0 |
| Poly(2,2'-bipyrrolidine bispropanoic acid-butyl diamine) | 12 | 314 | — | — | — | >3200 | 128.0 | 128.0 | 128.0 | 128.0 | 128.0 |
| Poly(2,2'-bipyrrolidine bispropanoic acid-ethyl diamine) | 73 | 292 | — | — | — | >3200 | 128.0 | 128.0 | 128.0 | 128.0 | 128.0 |
| Poly(2,2'-bipyrrolidine bispropanoic acid-penta diamine) | 21 | 297 | — | — | — | >3200 | 128.0 | 128.0 | 128.0 | 128.0 | 128.0 |
| 4,4'-trimethylene dipiperidine-bispropanoic acid-diamino-propane pentamer | >512 | >512 | — | — | 259.0 | >3200 | 16.0 | 1.0 | 16.0 | >128 | 64.0 |
| 4,4'-trimethylene dipiperidine-bispropanoic acid-diamino-propane heptamer | 190 | >512 | — | — | 418.0 | >3200 | 2.0 | 1.0 | 8.0 | >128 | 128.0 |
| Poly(4,4-trimethylene dipiperidine-bispropanoic acid-diamino-propane) (guanidine ended) | 2 | 4 | — | — | 10 | 738.0 | 2.0 | 0.3 | 2.0 | 8.0 | 8.0 |
| 40 mol % modified Poly(4,4-trimethylene dipiperidine bispropanoic acid-diamino-propane) | 3 | 5 | — | — | 7 | 757.0 | 0.5 | 0.1 | 1.0 | 8.0 | 4.0 |

TABLE 2-continued

In vitro Results of Representative Amine Functional Polyamides
Cytotoxicity Assay [Kidney Epithelial and Human Dermal Fibroblast $IC_{50}$ and $LC_{50}$],
Erythrocyte Lysis Assay [Hemolysis $IC_{50}$],
and MIC values against Clinically Relevant Microorganisms

| Polymer Description | Cytotoxicity (Kidney Epithelial $IC_{50}$) | Cytotoxicity (Kidney Epithelial $LC_{50}$) | Cytotoxicity (Human Dermal Fibroblast $IC_{50}$) | Cytotoxicity (Human Dermal Fibroblast $LC_{50}$) | Lung Epi $IC_{50}$ | Erythrocyte Lysis (Hemolysis $IC_{50}$) | Staphylococcus aureus subsp. aureus (MIC) | Staphylococcus epidermis (MIC) | Escherichia coli (MIC) | Pseudomonas aeruginosa (MIC) | Haemophilus influenzae (MIC) |
|---|---|---|---|---|---|---|---|---|---|---|---|
| 40 mol % modified Poly(4,4-trimethylene dipiperidine-bispropanoic acid-diaminopropane) | 2 | 6 | — | — | 8 | 118.0 | 1.0 | 0.3 | 2.0 | 8.0 | 4.0 |
| Poly(4,4'-trimethylene dipiperidine-bispropanoic acid-N-glycidol diethylene triamine) | >512 | >512 | — | — | >512 | >3200 | >128 | >128 | >128 | >128 | >128 |
| Poly(4,4'-trimethylene dipiperidine-bispropanoic acid-N-glycidol diethylene triamine) | 72 | 178 | — | — | >512 | >3200 | >128 | >128 | >128 | >128 | >128 |
| Poly(4,4'-trimethylene dipiperidine-bispropanoic acid-N-glycidol dipropylene triamine) | 70 | 161 | — | — | >512 | >3200 | >128 | 32.0 | >128 | >128 | >128 |
| Poly(4,4'-trimethylene-dipiperidine bisethylacrylamide-co-1,3-diamine propane) | 20 | 32 | — | — | — | 267.0 | >128 | 8.0 | 64.0 | 128.0 | >128 |
| Poly(4,4'-trimethylene-dipiperidine bisethylacrylamide-co-1-amino-3-guanidine propane) | 22 | 34 | — | — | — | 122.0 | 16.0 | 8.0 | 16.0 | 64.0 | >128 |
| 4,4-trimethylene dipiperidine-bispropanoic acid-1-amino-3-guanidine propane | >512 | >512 | — | — | — | >3200 | >128 | >128 | >128 | >128 | >128 |
| Poly(4,4-trimethylene dipiperidine-bispropanoic acid-diaminopropane), 1400 | 82 | 499 | — | — | — | >3200 | 4.0 | 4.0 | 16.0 | >128 | 128.0 |

TABLE 2-continued

In vitro Results of Representative Amine Functional Polyamides
Cytotoxicity Assay [Kidney Epithelial and Human Dermal Fibroblast $IC_{50}$ and $LC_{50}$],
Erythrocyte Lysis Assay [Hemolysis $IC_{50}$],
and MIC values against Clinically Relevant Microorganisms

| Polymer Description | Cytotoxicity (Kidney Epithelial $IC_{50}$) | Cytotoxicity (Kidney Epithelial $LC_{50}$) | Cytotoxicity (Human Dermal Fibroblast $IC_{50}$) | Cytotoxicity (Human Dermal Fibroblast $LC_{50}$) | Lung Epi $IC_{50}$ | Erythrocyte Lysis (Hemolysis $IC_{50}$) | Staphylococcus aureus subsp. aureus (MIC) | Staphylococcus epidermis (MIC) | Escherichia coli (MIC) | Pseudomonas aeruginosa (MIC) | Haemophilus influenzae (MIC) |
|---|---|---|---|---|---|---|---|---|---|---|---|
| Poly(4,4'-trimethylene-dipiperidine bisethylacrylamide-1,3-diamine propane)-co-Poly(4,4'-trimethylene-dipiperidine bisethylacrylamide-1-aminobutyl-3-carbamoyl-pyridinium) | 5 | 10 | — | — | — | 44.0 | 32.0 | 2.0 | 8.0 | 16.0 | >128 |
| Poly(4,4'-trimethylene-dipiperidine bisethylacrylamine-1-aminobutyl-3-carbamoyl-pyridinium) | 11 | 16 | — | — | — | 83.0 | >128 | 32.0 | 64.0 | >128 | >128 |
| 40 mol % glycidol modified poly(4,4-trimethylene dipiperidine-bispropanoic acid-diamino-propane), 4700 | 1 | 2 | — | — | — | 287.0 | 1.0 | 0.5 | 2.0 | 4.0 | 8.0 |
| Guanidine terminated Poly(4,4-trimethylene dipiperidine-bispropanoic acid-diamino-propane), 4700 | 1 | 4 | — | — | — | 334.0 | 1.0 | 0.5 | 2.0 | 4.0 | 8.0 |
| Guanidine terminated poly(4,4-trimethylene dipiperidine-bispropanoic acid-diamino-propane), 7700 | 1 | 1 | — | — | — | 18.0 | 1.0 | 0.5 | 2.0 | 4.0 | 8.0 |
| Carboxy terminated Poly(4,4-trimethylene dipiperidine-bispropanoic acid-diamino-propane) | 43 | >512 | — | — | — | >3200 | 64.0 | 32.0 | 128.0 | >128 | >128 |
| Methyl ester terminated Poly(4,4-trimethylene dipiperidine-bispropanoic acid-diamino-propane) | 1.5 | 4 | — | — | — | 152.0 | 4.0 | 0.5 | 4.0 | 16.0 | 8.0 |

TABLE 2-continued

In vitro Results of Representative Amine Functional Polyamides
Cytotoxicity Assay [Kidney Epithelial and Human Dermal Fibroblast $IC_{50}$ and $LC_{50}$],
Erythrocyte Lysis Assay [Hemolysis $IC_{50}$],
and MIC values against Clinically Relevant Microorganisms

| Polymer Description | Cytotoxicity (Kidney Epithelial $IC_{50}$) | Cytotoxicity (Kidney Epithelial $LC_{50}$) | Cytotoxicity (Human Dermal Fibroblast $IC_{50}$) | Cytotoxicity (Human Dermal Fibroblast $LC_{50}$) | Lung Epi $IC_{50}$ | Erythrocyte Lysis (Hemolysis $IC_{50}$) | Staphylococcus aureus subsp. aureus (MIC) | Staphylococcus lococcus epidermis (MIC) | Escherichia coli (MIC) | Pseudomonas aeruginosa (MIC) | Haemophilus influenzae (MIC) |
|---|---|---|---|---|---|---|---|---|---|---|---|
| Guanidine terminated Poly(4,4-trimethylene dipiperidine-bispropanoic acid-diamino-propane), 2200 | 93 | 169 | — | — | — | >3200 | 1.0 | 0.3 | 2.0 | 64.0 | 16.0 |
| Poly(4,4-trimethylene dipiperidine-bispropanoic acid-aminomethyl benzene) | 4 | 10 | — | — | — | 14.0 | 64.0 | 8.0 | 16.0 | 16.0 | >128 |
| 4,4 trimethylene dipiperidine-bispropanoic acid-diamino-propane | >512 | >512 | — | — | — | >3200 | >128 | >128 | >128 | >128 | >128 |
| Poly[4,4-trimethylene dipiperidine-bispropanoic acid-(1-amino methyl-4-guanidine-methyl benzene)] | 3 | 5 | — | — | — | 52.0 | 4.0 | 64.0 | 8.0 | 64.0 | >128 |
| 4-guanidino-benzene terminated Poly(4,4-trimethylene dipiperidine-bispropanoic acid-diamino-propane) | 6 | 12 | — | — | — | 1142 | 4.0 | 2.0 | 4.0 | 64.0 | 32.0 |
| Poly(4,4-trimethylene dipiperidine-bispropanoic acid-diamino-propane), <10K | 29.6 | 110.1 | — | — | — | >3200 | 1.0 | 0.5 | 4.0 | 64.0 | 16.0 |

—indicates not tested.

Example 1-5

Inhibition of Pseudomonas aeruginosa in Cystic Fibrosis Bronchial Epithelial Cells Cystic fibrosis bronchial epithelial (CFBE) cells were grown in 12-well plates for 7-9 days. The cells were washed twice with imaging medium before Pseudomonas aeruginosa (mucoid strain, SMC 1585) was inoculated into each well at a multiplicity of infection (MOI) of ~30 (~6×10$^6$ cfu/well). The plates were incubated at 37° C., 5% $CO_2$ for 1 hour to allow bacterial attachment to the airway cells. The supernatant was then replaced with imaging medium containing 0.4% arginine and then incubated for 5 hours to form biofilms on CFBE cells. To estimate the efficacy of antimicrobial polymer treatment in preformed biofilms, the plates were washed twice with imaging medium and antimicrobial agent (antimicrobial polymer or tobramycin [positive control]) were applied at designated concentrations to disrupt established biofilms for 16 hours. The supernatant was then removed and washed twice with imaging medium. CFBE cells were lysed with 0.1% Triton X-100 for approximately 15 minutes. The lysate was vortexed for 3 minutes before serial dilution and spot titration onto LB plates to determine the cfu/well. The bacterial strain was defined as 'susceptible' to the antibiotic treatment in the static co-culture model if the CFBE monolayers were not disrupted after overnight antibiotic treatment and there was more than a 2 $\log_{10}$ difference in cfu recovery between no treatment and antibiotic antimicrobial agent treatment.

To test the ability of antibiotics to prevent biofilm formation, these compounds were applied after the 1 hour period for bacterial attachment. The plates were incubated for 5 hours, and cfu/well was determined as described above. The detection limit of the static co-culture assay was 200 cfu/well. All experiments were performed at least three times. The susceptibility of *Pseudomonas aeruginosa* biofilm to Poly(4,4-trimethylene dipiperidinebispropanoic acid-diaminopropane) <10K is displayed in Figure I below.

Example 2

In vivo Studies

Example 2-1

Toxicity—Maximum Tolerated Dose

Acute, 24 hour, toxicity studies to determine the maximum tolerated dose of a compound were carried out in male rats and mice of approximately 8-10 weeks of age. Animals were housed singly in standard polycarbonate cages and fed normal chow diets. Following one week of acclimation, compounds were administered in a single intraperitoneal (I.P.) or intravenous (I.V.) dose, typically in a PBS vehicle. The doses generally ranged from 1 mg/kg to as high as 400 mg/kg. Animals were observed for signs of pain, distress, and local or systemic signs of toxicity for one hour post-dosing, and then in 1 hour intervals for 6 hours after dosing. The following day at 24 hours post-dose, the animals were sacrificed and blood removed for serum chemistry analysis. Serum chemistry analyses performed include: ALT, AST, Creatinine and Urea Nitrogen. Major organs were also examined for abnormal signs.

Table 3 displays the Maximum Tolerated Dose (MTD) for select test compounds at select routes of administration.

TABLE 3

| Maximum Tolerated Dose (MTD) | | | |
|---|---|---|---|
| Treatment | Animal Model | Route of Administration | MTD |
| Poly (4,4'-trimethylene dipiperidine bispropanoic acid-co-1,3-diamino propane), MW = 4,700 | Rat | I.P. | 5 mg/kg |
| Poly (4,4'-trimethylene dipiperidine bispropanoic acid-co-1,3-diamino propane), MW = 2,500 | Rat | I.P. | 5 mg/kg |
| Poly(4,4-trimethylene dipiperidinebispropanoic acid-diaminopropane), MW < 10K | Mice | I.P. | 5 mg/kg |
| Poly (4,4'-trimethylene dipiperidine bispropanoic acid-co-1,3-diamino propane), MW = 2,500 | Mice | I.V. | 40 mg/kg |

Example 2-2

Efficacy—Surgical Site Infection

The test compound, poly(4,4-trimethylene dipiperidinebispropanoic acid-diaminopropane) modified with 40 mol % of glycidol, was evaluated for anti-infective activity against *Staphylococcus aureus*, Methicillin Resistant (MRSA) and *Escherichia coli* (*E. coli*) in mice. Male ICR mice weighing approximately 22 g were used to evaluate the anti-infective activity against each bacterium.

Example 2-2(a)

MRSA

Five groups of 10 male mice were inoculated intraperitoneally with a $LD_{90-100}$ of MRSA ($1.90 \times 10^8$ CFU/mouse) suspended in 0.5 mL of brain heart infusion (BHI) broth containing 5% mucin. One hour after bacteria inoculation, groups of 10 animals were intraperitoneally administered one of the following:
  0.2 mg/kg poly(4,4-trimethylene dipiperidinebispropanoic acid-diaminopropane) modified with 40 mol % of glycidol suspended in 0.9% NaCl,
  5 mg/kg poly(4,4-trimethylene dipiperidinebispropanoic acid-diaminopropane) modified with 40 mol % of glycidol suspended in 0.9% NaCl,
  1 mg/kg ofloxacin,
  3 mg/kg ofloxacin, and
  5 mL/kg vehicle (0.9% NaCl).

Mortality was recorded once daily for 7 days and an increase of survival relative to vehicle control group was evaluated.

Table 4 displays the results against MRSA for the test compounds.

TABLE 4

| MRSA Activity | | | |
|---|---|---|---|
| Treatment | Dose | Animals Dosed (N) | Survival (n/N) | Survival Increase (%) |
| Vehicle | 5 mL/kg | 10 | 0/10 | — |
| Poly(4,4-trimethylene dipiperidinebispropanoic acid-diaminopropane) modified with 40 mol % of glycidol | 0.2 mg/kg | 10 | 1/10 | 10% |
|  | 5 mg/kg | 10 | 6/10 | 60%* |

*Survival increase ≥50% indicates significant anti-microbial effect

Example 2-2(b)

E. coli

Five groups of 10 male mice were inoculated intraperitoneally with a $LD_{90-100}$ of *E. coli* ($2.20 \times 10^5$ CFU/mouse) suspended in 0.5 mL of BHI broth containing 5% mucin. One hour after bacteria inoculation, groups of 10 animals were intraperitoneally administered one of the following:
  0.2 mg/kg poly(4,4-trimethylene dipiperidinebispropanoic acid-diaminopropane) modified with 40 mol % of glycidol suspended in 0.9% NaCl,
  5 mg/kg poly(4,4-trimethylene dipiperidinebispropanoic acid-diaminopropane) modified with 40 mol % of glycidol suspended in 0.9% NaCl,
  0.3 mg/kg gentamicin,
  1 mg/kg gentamicin, and
  5 mg/kg vehicle (0.9% NaCl).

Mortality was recorded once daily for 7 days and an increase of survival relative to vehicle control group was evaluated.

Table 5 displays the results against *E. coli* for the test compounds.

TABLE 5

E. coli Activity

| Treatment | Dose | Animals Dosed (N) | Survival (n/N) | Survival Increase (%) |
|---|---|---|---|---|
| Vehicle | 5 mL/kg | 10 | 0/10 | — |
| Poly(4,4-trimethylene dipiperidinebispropanoic acid-diaminopropane) modified with 40 mol% of glycidol | 0.2 mg/kg | 10 | 0/10 | 0% |
| | 5 mg/kg | 10 | 8/10 | 80%* |

*Survival increase ≥50% indicates significant anti-microbial effect

The test compound, poly(4,4-trimethylene dipiperidinebispropanoic acid-diaminopropane) modified with 40 mol % of glycidol, afforded significant anti-microbial protection, exhibiting 60% and 80% increase in survival rate in MRSA and E. coli infected mouse models.

Example 2-3

Efficacy—Mucositis

The goal of this study was to examine the role of schedule and route of administration on the observed efficacy of poly (4,4-trimethylene dipiperidinebispropanoic acid-diaminopropane) (1 mg/mL) on the frequency, severity and duration of oral mucositis induced by acute radiation. Male LVG Syrian Golden Hamsters, aged 5 to 6 weeks with an average body weight of 86.3 g at study commencement were used to evaluate the activity of each compound against radiation induced oral mucositis. Study endpoints were mucositis score, weight change and survival.

Male Syrian Golden Hamsters were randomly and prospectively divided into treatment groups of seven (7) animals per group (test article) and one group of ten (10) animals (control).

On day 0, all animals were given an acute radiation dose of 40 Gy directed to their left buccal cheek pouch. On day 0, animals were dosed topically once. From day 0 to day 20, 0.5 mL doses were applied topically to the left buccal pouch three times per day.

To evaluate mucositis severity, animals were anesthetized with an inhalation anesthetic, and the left cheek pouch everted. Mucositis was scored visually by comparison to a validated photographic scale; the scale ranges from 0 for normal, to 5 for severe ulceration. A descriptive version of the mucositis scoring scale used in this study is presented in Table 6.

TABLE 6

Mucositis Scoring Scale

| Score | Description: |
|---|---|
| 0 | Pouch completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray appearance due to pseudomembrane formation. Cumulative size of ulcers should equal about ¼ of the pouch. Severe erythema and vasodilation. |
| 4 | Cumulative size of ulcers should equal about ½ of the pouch. Loss of pliability. Severe erythema and vasodilation. |
| 5 | Virtually all of pouch is ulcerated. Loss of pliability (pouch can only partially be extracted from mouth. |

A score of 1 or 2 represent a mild stage of injury, a score of 3, 4 or 5 indicates moderate to severe mucositis. Following visual scoring, a digital photograph was taken of each animal's mucosa using a standardized technique. At the conclusion of the experiment, all images were randomly numbered and graded in blinded fashion by at least two independent trained observers using the above-described scale (blinded scoring).

Animal deaths were evaluated during the course of the study. In the model, deaths are most commonly attributable to adverse effects associated with anesthesia typically occurring at the time of radiation, or toxicity of the experimental compound. There were no deaths associated with the experimental compounds.

Weight change was also evaluated as it represents a secondary method of examining potential toxicities of experimental treatments. Animals were weighed daily throughout the study; weight changes were similar in all groups. The mean percent weight gain during the study is provided in Table 7.

To evaluate the significance of these differences, the mean area under the curve (AUC) was calculated for each animal from the percent weight gain data, and the means and standard errors were plotted. Using a one way ANOVA, no statistically significant difference in weight change was observed in any of the groups.

To evaluate efficacy, the mean group mucositis scores were compared to the control group in each experiment. A clinical mucositis score of 3 in hamsters indicates the presence of an ulcer. Ulceration is the point in the development of mucositis where the physical integrity of the oral mucosa is breached. In the clinic, a patient presenting with severe oral ulcerations may require hospitalization for analgesic, narcotic and/or antibiotic therapies or fluid support. The average cost to the healthcare system is significant. Advanced mucositis in humans (with ulcerative sores, correlating to a score of 3 or greater) often requires the interruption of therapy for patients receiving radiation and, if sepsis occurs, these patients risk death. A therapeutic that significantly reduces the time that a patient with oral mucositis had ulcers would be of great value to the clinician. The cumulative number of days that an animal had a score of 3 or greater was determined due to its clinical significance.

The significance of group differences in scores of 3 or greater was determined using Chi-squared ($\chi^2$) difference analysis for the total number of animal days with a score of 3 or higher over the course of the entire study; these results are presented in Table 7. The severity and course of mucositis was favorably attenuated the in the poly(4,4-trimethylene dipiperidinebispropanoic acid-diaminopropane) group.

TABLE 7

Mucositis Safety and Efficacy

| Group | Dose (Concentration) | % Weight Gain (Days 0 to 20) | % Animal Days with Mucositis Score ≥ 3 |
|---|---|---|---|
| Control topical, tid | 0.5 mL | 41.6 | 41.3 |
| Poly(4,4-trimethylene dipiperidinebispropanoic acid-diaminopropane), topical, tid | 0.5 mL (1 mg/mL) | 34.2 | 28.6 |

Example 3

Synthesis of Amine Functional Polyamides

Example 3-1

Synthesis of 4,4'-trimethylene dipiperidine bispropanoic acetate

To 5.0 g of 4,4'-trimethylene dipiperidine in 20 mL of methanol solution (20 mL), 4.6 g of methyl acrylate was added drop-wise. The resulting reaction mixture was stirred at room temperature for 16 hours. The solvent was removed under reduced pressure and the residue was purified by column chromatography using a gradient solvent system comprising of from 100% hexane to 100% ethyl acetate. Removal of the solvent under reduced pressure yielded 7 g of the desired product as a white solid.

Example 3-2

Synthesis of 4,4'-dipiperidine bispropanoic acetate

To 10.0 g of 4,4'-dipiperidine HCl dissolved in 80 mL of methanol was added 12.6 g of potassium carbonate. The reaction mixture was stirred at room temperature for 3 hours, at which time 8.03 g of methyl acrylate was added slowly. The resulting reaction solution was then stirred at room temperature for 18 hours. The reaction mixture was filtered and the filtrate was evaporated to dryness under reduced pressure. The residue was treated with 300 mL of ethyl acetate. The resulting suspension was stirred at room temperature for 2 hours followed by filtration. The filtrate was evaporated to dryness under reduced pressure. The resulting mass was dried at room temperature under the vacuum to give 11.34 g of the desired product as an off white solid.

Example 3-3

Synthesis of Piperazine Bispropanoic Acetate

To 10 g of piperazine hexahydate dissolved in 40 mL of methanol was added 9.97 g of methyl acrylate in a drop-wise manner. The reaction mixture was stirred at room temperature for 18 hours. At the end of this time, the reaction mixture was evaporated to dryness under reduced pressure. The residue was recrystallized from hexane/methylene chloride (1:1 v/v). After filtration and drying at room temperature under reduced pressure, 12.2 g of the desired product was obtained as a white solid.

Example 3-4

Synthesis of 1,1'-diacryl-4,4'-trimethylene dipiperidine

To 3.8 g of acryloyl chloride dissolved in 50 mL of dichloromethane was added a solution of 4.0 g of 4,4-trimethylene dipiperidine dissolved in 20 mL dichloromethane in a drop-wise manner at 0° C. To this solution was added 4.23 g of triethyl amine slowly with a syringe. The resulting reaction mixture was stirred for 18 hours and was allowed to warm to room temperature. The reaction mixture was filtered and the filtrate was collected. After removing the solvent under reduced pressure, the residue was treated with 100 mL of ethyl acetate. The solution was extracted with 1M HCl (1×100 mL), saturated NaHCO$_3$ (2×100 mL), and finally with brine (2×100 mL). The organic layer was collected and dried over Na$_2$SO$_4$. After filtration, the filtrate was evaporated to dryness under reduced pressure. The residue was purified by column chromatography using a gradient solvent system from 100% hexane to 100% ethyl acetate. Upon removal of the solvent, 3 g of the desired product was obtained as viscous oil.

Example 3-5

Synthesis of 2,2'-bipyrrolidine bispropanoic acetate

To a solution of 5 g of 2,2'-bipyrrolidine in 20 mL of methanol was added 6.9 g of methyl acrylate (6.9 g, 80 mmol) in a drop-wise manner. The resulting reaction mixture was stirred at room temperature for 16 hours. The reaction mixture was evaporated to dryness yielding 10 g of the desired product as viscous oil.

Example 3-6

Synthesis of poly(4,4'-trimethylene dipiperidine bispropanoic acid-co-1,3-diamino propane)

The reaction mixture consisting of 1 g of 4,4'-trimethylene dipiperidine bispropanoic acetate (Example 3-1) and 0.387 g of 1,3-diamino propane was heated at 100° C. under nitrogen atmosphere for 18 hours. The resulting product was dissolved in 5 mL of dichloromethane and was poured into 50 mL of ethyl acetate. After filtering off the solvent, the residue was dissolved in 20 mL of deionized (DI) water. The pH of the solution was brought to 2 by addition of HCl. The resulting solution was dialyzed against DI water for 24 hours using a dialysis membrane of molecular weight cut off of 1000 Dalton. The solution remaining in the dialysis bag was dried by lyophilization yielding 90 mg of the desired product as a light yellow solid.

Example 3-7

Synthesis of poly(4,4'-trimethylene dipiperidine bispropanoic acid-co-diamino ethane)

The reaction mixture containing 0.5 g of 4,4'-trimethylene dipiperidine bispropanoic acetate (Example 3-1) and 0.157 g of diamino ethane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 50 mg of the desired product as a light yellow solid.

Example 3-8

Synthesis of poly(4,4'-trimethylene dipiperidine bispropanoic acid-co-1,4-diamino butane)

The reaction mixture containing 0.5 g of 4,4'-trimethylene dipiperidine bispropanoic acetate and 0.23 g of 1,4-diamino butane was stirred at 100° C. under nitrogen atmosphere for 18 hours. The resulting product was dissolved in 5 mL of CH$_2$Cl$_2$ and then precipitated in 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 60 mg of the desired product as a light yellow solid.

Example 3-9

Synthesis of poly(4,4'-trimethylene dipiperidine bispropanoic acid-co-1,2-bis(2-aminoethoxy)ethane The reaction mixture containing 0.5 g of 4,4'-trimethylene dipiperidine bispropanoic acetate and 0.26 g of 1,2-bis(2-aminoethoxy)ethane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 60 mg of the desired product as a light yellow solid.

Example 3-10

Synthesis of poly(4,4'-trimethylene dipiperidine bispropanoic acid-co-1,4-bis(aminomethyl)benzene The reaction mixture containing 0.5 g of 4,4'-trimethylene dipiperidine bispropanoic acetate and 0.7 g of 1,4-bis(aminomethyl)benzene (0.7 g, 5.1 mmol) was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 40 mg of the desired product as a light yellow solid.

Example 3-11

Synthesis of poly(4,4'-trimethylene dipiperidine bispropanoic acid-co-2,2'diamino diethylamine The reaction mixture containing 0.5 g of 4,4'-trimethylene dipiperidine bispropanoic acetate and 0.35 g of 2,2'diamino diethylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 63 mg of the desired product as a light yellow solid.

Example 3-12

Synthesis of poly(4,4'-trimethylene dipiperidine bispropanoic acid-co-N-methyl-2,2'diamino diethylamine The reaction mixture containing 1 g of 4,4'-trimethylene dipiperidine bispropanoic acetate and 0.61 g of N-methyl-2, 2'diamino diethylamine (0.61 g, 5.2 mmol) was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 130 mg of the desired product as a light yellow solid.

Example 3-13

Synthesis of poly(4,4'-trimethylene dipiperidine bispropanoic acid-co-N-(3-aminopropyl)-1,3-propane diamine The reaction mixture containing 1 g of 4,4'-trimethylene dipiperidine bispropanoic acetate and 0.68 g of N-(3-aminopropyl)-1,3-propane diamine (0.68 g, 5.2 mmol) was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 180 mg of the desired product as a light yellow solid.

Example 3-14

Synthesis of poly(4,4'-trimethylene dipiperidine bispropanoic acid-co-3,3'-diamino-N-methyl dipropylamine The reaction mixture containing 1 g of 4,4'-trimethylene dipiperidine bispropanoic acetate and 0.76 g of 3,3'-diamino-N-methyl dipropylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 110 mg of the desired product as a light yellow solid.

Example 3-15

Synthesis of poly(4,4'-trimethylene dipiperidine bispropanoic acid-co-1,3-diamino-2-propanol The reaction mixture containing 1 g of 4,4'-trimethylene dipiperidine bispropanoic acetate and 0.47 g of 1,3-diamino-2-propanol (0.47 g, 5.2 mmol) was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 60 mg of the desired product as a light yellow solid.

Example 3-16

Synthesis of poly(4,4'-trimethylene dipiperidine bispropanoic acid-co-4-(4-amino-butoxyl)-butyl amine 4-(4-amino-butoxyl)-butyl amine HCl salt (1 g) was dissolved in 20 mL of methanol. To this solution 0.72 g of aqueous sodium hydroxide solution (50% w/w)) was added. The reaction mixture was stirred at room temperature for 1 hour. After filtering off the solids, the filtrate was evaporated to dryness. The residue was treated with 20 mL of ethanol. The reaction mixture was filtered and the filtrate was evaporated to dryness yielding 0.55 g of an off white solid. This solid was combined with 0.75 g of 4,4'-trimethylene dipiperidine bispropanoic acetate and the resulting reaction mixture was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 90 mg of the desired product as a light yellow solid.

Example 3-17

Synthesis of poly(4,4'-trimethylene dipiperidine bispropanoic acid-co-3,5-diamino-1,2,4-triazol The reaction mixture containing 1 g of 4,4'-trimethylene dipiperidine bispropanoic acetate and 0.31 g of 3,5-diamino-1,2,4-triazole was treated with 1 mL of DMSO. The resulting reaction mixture was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 10 mg of the desired product as a light yellow solid.

Example 3-18

Synthesis of poly(piperazine bispropanoic acid-co-diamino ethane)

The reaction mixture containing 1 g of piperazine bispropanoic acetate (Example 3-3) and 0.47 g of diamino ethane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 10 mg of the desired product as a light yellow solid.

Example 3-19

Synthesis of poly(piperazine bispropanoic acid-co-1,3-diamino propane)

The reaction mixture containing 1 g of piperazine bispropanoic acetate (Example 3-3) and 0.5 g of 1,3-diamino propane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 30 mg of the desired product as a light yellow solid.

Example 3-20

Synthesis of poly(piperazine bispropanoic acid-co-1,4-diamino butane)

The reaction mixture containing 1 g of piperazine bispropanoic acetate (Example 3-3) and 0.6 g of 1,4-diamino butane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 60 mg of the desired product as a light yellow solid.

Example 3-21

Synthesis of poly(piperazine bispropanoic acid-co-1,2-bis(2-aminoethoxy)ethane

The reaction mixture containing 1 g of piperazine bispropanoic acetate (Example 3-3) and 1.15 g of 1,2-bis(2-aminoethoxy)ethane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 30 mg of the desired product as a light yellow solid.

Example 3-22

Synthesis of poly(piperazine bispropanoic acid-co-2,2'diamino diethylamine

The reaction mixture containing 1 g of piperazine bispropanoic acetate (Example 3-3) and 0.8 g of 2,2'-diamino diethylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 60 mg of the desired product as a light yellow solid.

Example 3-23

Synthesis of poly(piperazine bispropanoic acid-co-N-methyl-2,2'diamino diethylamine The reaction mixture containing 1 g of piperazine bispropanoic acetate (Example 3-3) and 0.9 g of N-methyl-2,2'-diamino diethylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 50 mg of the desired product as a light yellow solid.

Example 3-24

Synthesis of poly(piperazine bispropanoic acid-co-N-(3-aminopropyl)-1,3-propane diamine The reaction mixture containing 1 g of piperazine bispropanoic acetate (Example 3-3) and 1.02 g of N-(3-aminopropyl)-1,3-propane diamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 90 mg of the desired product as a light yellow solid.

Example 3-25

Synthesis of poly(piperazine bispropanoic acid-co-3,3'-diamino-N-methyl dipropylamine The reaction mixture containing 1 g of piperazine bispropanoic acetate (Example 3-3) and 1.12 g of 3,3'-diamino-N-methyl dipropylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 120 mg of the desired product as a light yellow solid.

Example 3-26

Synthesis of poly(4,4'-dipiperidine bispropanoic acid-co-diamino ethane

The reaction mixture containing 1 g of 4,4'-dipiperidine bispropanoic acetate (Example 3-2) and 0.31 g of diamino ethane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 90 mg of the desired product as a light yellow solid.

Example 3-27

Synthesis of poly(4,4'-dipiperidine bispropanoic acid-co-1,3-diamino propane

The reaction mixture containing 1 g of 4,4'-dipiperidine bispropanoic acetate (Example 3-2) and 0.38 g of 1,3-diamino propane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 60 mg of the desired product as a light yellow solid.

Example 3-28

Synthesis of poly(4,4'-dipiperidine bispropanoic acid-co-1,4-diamino butane

The reaction mixture containing 1 g of 4,4'-dipiperidine bispropanoic acetate (Example 3-2) and 0.45 g of 1,4-diamino butane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 90 mg of the desired product as a light yellow solid.

Example 3-29

Synthesis of poly(4,4'-dipiperidine bispropanoic acid-co-1,2-bis(2-aminoethoxy)ethane The reaction mixture containing 1 g of 4,4'-dipiperidine bispropanoic acetate (Example 3-2) and 0.76 g of 1,2-bis(2-aminoethoxy)ethane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 100 mg of the desired product as a light yellow solid.

Example 3-30

Synthesis of poly(4,4'-dipiperidine bispropanoic acid-co-2,2'diamino diethylamine The reaction mixture containing 1 g of 4,4'-dipiperidine bispropanoic acetate and 0.45 g of 2,2'diamino diethylamine was stirred at 100° C. under nitrogen atmosphere for 18 hours.

Example 3-31

Synthesis of poly(4,4'-dipiperidine bispropanoic acid-co-N-methyl-2,2'diamino diethylamine The reaction mixture containing 1 g of 4,4'-dipiperidine bispropanoic acetate and 0.52 g of N-methyl-2,2'diamino diethylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 480 mg of the desired product as a light yellow solid.

Example 3-32

Synthesis of poly(4,4'-dipiperidine bispropanoic acid-co-N-(3-aminopropyl)-1,3-propane diamine The reaction mixture containing 1 g of 4,4'-dipiperidine bispropanoic acetate and 0.58 g of N-(3-aminopropyl)-1,3-propane diamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 540 mg of the desired product as a light yellow solid.

Example 3-33

Synthesis of poly(4,4'-dipiperidine bispropanoic acid-co-3,3'-diamino-N-methyl dipropylamine The reaction mixture containing 1 g of 4,4'-dipiperidine bispropanoic acetate and 0.64 g of 3,3'-diamino-N-methyl dipropylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 420 mg of the desired product as a light yellow solid.

The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 310 mg of the desired product as a light yellow solid.

Example 3-34

Synthesis of Poly(1,1'-diacryl-4,4'-trimethylene dipiperidine-co-1,3-diaminopropane The reaction mixture containing 1 g of 1,1'-diacryl-4,4'-trimethylene dipiperidine, 0.35 g 1,3-diamino propane and 1 mL of methanol was stirred at room temperature for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 640 mg of the desired product as a light yellow solid.

Example 3-35

Synthesis of poly(1,1'-diacryl-4,4'-trimethylene dipiperidine-co-N,N'-dimethyl-1,3-propanediamine The reaction mixture containing 1 g of 1,1'-diacryl-4,4'-trimethylene dipiperidine, 0.36 g of N,N'-dimethyl-1,3-propanediamine and 1 mL of methanol was stirred at 60° C. for 24 hours. The solvent was removed under reduced pressure and the residue was dissolved in 20 mL of DI water. The pH of the solution was adjusted to 2 by adding HCl. The polymer solution dialyzed against DI water using a dialysis membrane of molecular weight cut off of 1000 Dalton. The solution remaining in the dialysis membrane was lyophilized to dryness yielding 180 mg of the desired product as a light yellow solid.

Example 3-36

Synthesis of poly(1,1'-diacryl-4,4'-trimethylene dipiperidine-co-4,4'-trimethylene dipiperidine The reaction mixture containing 1 g of 1,1'-diacryl-4,4'-trimethylene dipiperidine, 0.99 g of 4,4'-trimethylene dipiperidine, 1 mL of methanol was stirred at 60° C. for 12 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 220 mg of the desired product as a light yellow solid.

Example 3-37

Synthesis of poly(1,1'-diacryl-4,4'-trimethylene dipiperidine-co-piperazine

The reaction mixture containing 1 g of 1,1'-diacryl-4,4'-trimethylene dipiperidine, 0.91 g of piperazine hexahydrate and 1 mL of methanol was stirred at 60° C. for 12 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 80 mg of the desired product as a light yellow solid.

Example 3-38

Synthesis of poly(1,1'-diacryl-4,4'-trimethylene dipiperidine-co-4,4'-bipiperidine)

A solution containing 1.14 g of 4,4'-dipiperidine HCl and 5 mL of methanol was treated with 1.14 g of potassium carbonate. The reaction mixture was stirred at room temperature for 2 hours. The reaction mixture was filtered and the filtrate was combined with 1 g of 1,1'-diacryl-4,4'-trimethylene dipiperidine dissolved in 3 mL of methanol. The resulting reaction mixture was stirred at 60° C. for 15 hours. The resulting product was poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 140 mg of the desired product as a light yellow solid.

Example 3-39

Synthesis of poly(1,1'diacryl-4,4'-trimethylene dipiperidine-co-histamine)

The reaction mixture containing 1 g of 1,1'-diacryl-4,4'-trimethylene dipiperidine, 0.5 g of histamine and 1 mL of methanol was stirred at 60° C. for 18 hours. The resulting product was poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 120 mg of the desired product as a light yellow solid.

Example 3-40

Synthesis of poly(1,1'diacryl-4,4'-trimethylene dipiperidine-co-3-(dimethylamino)-1-propylamine)

The reaction mixture containing 1 g of 1,1'-diacryl-4,4'-trimethylene dipiperidine, 0.53 g of 3-(dimethylamino)-1-propylamine and 1 mL of methanol was stirred at 50° C. for 10 hours. The resulting product was poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 1 g of the desired product as a light yellow solid.

Example 3-41

Synthesis of poly(1,1'diacryl-4,4'-trimethylene dipiperidine-co-propyl amine)

The reaction mixture containing 0.64 g of 1,1'-diacryl-4,4'-trimethylene dipiperidine, 0.35 g of propyl amine, and 1 mL methanol was stirred at 60° C. for 20 hours. The resulting product was poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 740 mg of the desired product as a light yellow solid.

Example 3-42

Synthesis of poly(1,1'diacryl 4,4'-trimethylene dipiperidine-co-1-aminobutyl-3-carbamoyl pyridinium)

The reaction mixture containing 0.5 g of 1,1'-diacryl-4,4'-trimethylene dipiperidine, 0.35 g of 1-aminobutyl-3-carbamoyl pyridinium, and 3 mL of methanol was stirred at 50° C. for 20 hours. The resulting product was poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 20 mg of the desired product as a light yellow solid.

Example 3-43

Synthesis of poly(1,1'diacryl-4,4'-trimethylene dipiperidine-co-1-aminobutyl-3-carbamoyl pyridinium)-co-4,4'-trimethylene dipiperidine bispropanoic acid-2-dydroxy-1,3-diamino propane)

The reaction mixture containing 1.0 g of 1,1'-diacryl-4,4'-trimethylene dipiperidine, 0.36 g of 1-aminobutyl-3-carbamoyl pyridinium, 0.27 g of mono N-boc-1,3-diaminopropane, and 3 mL of methanol stirred at 50° C. for 20 hours. The reaction mixture was poured into 50 mL of ethyl acetate. The precipitate was isolated by filtration. The residue was washed with ethyl acetate (3×50 mL) and dried under reduced pressure.

Above product was dissolved in 5 mL of methanol and mixed with 0.5 g of 4,4'-trimethylene dipiperidine bispropanoic acid and 0.25 mL of concentrated HCl. The resulting reaction mixture was stirred at 50° C. for 6 hours. The resulting product was poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 210 mg of the desired product as a light yellow solid.

Example 3-44

Synthesis of poly(2,2'-bipyrrolidine bispropanoic acid-co-diamino ethane)

The reaction mixture containing 1.0 g of 2,2'-bipyrrolidine bispropanoic acetate and 0.38 g diamino ethane was stirred at 100° C. under nitrogen atmosphere for 20 hours. The resulting product was dissolved in 3 mL of methanol and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 10 mg of the desired product as a light yellow solid.

Example 3-45

Synthesis of poly(2,2'-bipyrrolidine bispropanoic acid-co-1,3-diamino propane)

The reaction mixture containing 1.0 g of 2,2'-bipyrrolidine bispropanoic acetate and 0.47 g of 1,3-diamino propane was stirred at 100° C. under nitrogen atmosphere for 20 hours. The resulting product was dissolved in 3 mL of methanol and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 540 mg of the desired product as a light yellow solid.

Example 3-46

Synthesis of poly(2,2'-bipyrrolidine bispropanoic acid-co-1,3-diamino butane)

The reaction mixture containing 1.0 g of 2,2'-bipyrrolidine bispropanoic acetate and 0.56 g of 1,4-diamino butane was stirred at 100° C. under nitrogen atmosphere for 20 hours. The resulting product was dissolved in 3 mL of methanol and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 380 mg of the desired product as a light yellow solid.

Example 3-47

Synthesis of poly(2,2'-bipyrrolidine bispropanoic acid-co-1,5-diamino pentane)

The reaction mixture containing 1.0 g of 2,2'-bipyrrolidine bispropanoic acetate and 0.65 g of 1,5-diamino pentane was stirred at 100° C. under nitrogen atmosphere for 20 hours. The resulting product was dissolved in 3 mL of methanol and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 10 mg of the desired product as a light yellow solid.

Example 3-48

Synthesis of poly(2,2'-bipyrrolidine bispropanoic acid-co-1,6-diamino hexane)

The reaction mixture containing 1.0 g of 2,2'-bipyrrolidine bispropanoic acetate and 0.74 g of 1,6-diamino hexane was stirred at 100° C. under nitrogen atmosphere for 20 hours. The resulting product was dissolved in 3 mL of methanol and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 10 mg of the desired product as a light yellow solid.

Example 3-49

Synthesis of poly(4,4-Trimethylene dipiperidine bispropanoic acid-co-4-(1,2-diol)-1,4,7-triazaheptane)

Example 3-49(a)

Synthesis of 4-(1,2-diol)-1,4,7-triazaheptane

In 5 mL of ethanol 1 g of 1,7-bis-Boc-1,4,7-triazaheptane and 0.3 g of glycidol were added and the reaction mixture was refluxed for 15 hours. The resulting product was purified by column chromatography using gradient solvent system in the range of 100% hexane to 100% yielding 0.4 g of 1,7-bis-boc-4-(1,2-diol)-1,4,7-triazaheptane. To 0.4 g of 1,7-bis-boc-4-(1,2-diol)-1,4,7-triazaheptane dissolved in 2 mL of methanol was added 0.3 mL of concentrated HCl. The reaction mixture was stirred at 50° C. for 24 hours. After removing the solvent under reduced pressure, the residue was dissolved in 10 mL of methanol:water (1:1 v/v). To this solution was added 5.0 g of Amberlyst OH 26 resin. After stirring at room temperature for 3 hours, the resin was filtered off. The solvent was evaporated under reduced pressure. The resulting oil was lyophilized to dry to give 0.15 g of the desired product as a viscous liquid.

Example 3-49(b)

Synthesis of poly(4,4-Trimethylene dipiperidine bispropanoic acid-co-4-(1,2-diol)-1,4,7-triazaheptane)

The reaction mixture containing 0.288 g of 4,4'-trimethylene dipiperidine bispropanoic acetate and 0.15 g of 4-(1,2-diol)-1,4,7-triazaheptane (Example 3-49(a)) stirred at 100° C. for 18 hours. The resulting product was dissolved in 3 mL of methanol and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 160 mg of the desired product as a light yellow solid.

Example 3-50

Synthesis of poly(4,4-trimethylene dipiperidine bispropanoic acid-co-4-(1,2-diol)-1,4,7-triazaheptane-co-1,3-diamino propane)

The reaction mixture containing 0.25 g of 4,4'-trimethylene dipiperidine bispropanoic acetate, 0.09 g of 4-(1,2-diol)-1,4,7-triazaheptane (Example 3-49(a)) and 0.05 g of 1,3-diamino propane stirred at 100° C. for 18 hours. The resulting product was dissolved in 3 mL of methanol and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Dalton. The solution remaining in the dialysis membrane was lyophilized to dryness yielding 150 mg of the desired product as a light yellow solid.

Example 3-51

Synthesis of poly(4,4-Trimethylene dipiperidine bispropanoic acid-co-5-(1,2-diol)-1,5,9-triazanonane)

Example 3-51(a)

Synthesis of 5-(1,2-diol)-1,5,9-triazanonane

The reaction mixture containing 1.5 g of 1,9-Bis-BOC-1, 5,9-triazanonane, 0.34 g of glycidol, and 10 mL of ethanol was refluxed for 15 hours. After removal of the solvent, the residue was purified by column chromatography using a gradient solvent system ranging from 100% hexane to 100% ethyl acetate) yielding 0.7 g of 1,9-bis-boc-5-(1,2-diol)-1,5, 9-triazanonane. To 0.7 g of 1,9-bis-boc-5-(1,2-diol)-1,5,9-triazanonane dissolved in 2 mL of methanol was added 0.25 mL of concentrated HCl and the reaction mixture stirred at 50° C. for 24 hours. After removal of the solvent under reduced pressure, the residue was dissolved in 10 mL of methanol/water (1:1) mixture and 5 g of Amberlyst OH 26 resin was added it. After stirring at room temperature for 3 hours, the resin was filtered off. The solvent was removed under reduced pressure and the residue was lyophilized to dryness yielding 0.28 g of the desired product as light yellow oil.

Example 3-51(b)

Synthesis of poly(4,4-Trimethylene dipiperidine bispropanoic acid-co-5-(1,2-diol)-1,5,9-triazanonane)

The reaction mixture containing 0.23 g of 4,4'-trimethylene dipiperidine bispropanoic acetate and 0.15 g of 5-(1,2-diol)-1,5,9-triazanonane was stirred at 100° C. for 18 hours. The resulting reaction mixture was dissolved in 5 mL of methanol and poured into 50 mL of ethyl acetate. After filtering off the solvent, the residue was dissolved in 20 mL of DI water. The pH of the solution was adjusted to 2 by adding dilute HCl and the solution subjected to centrifugation using with Microsep membrane filter with a molecular weight cut off of 1000 Dalton. The fraction with molecular weight higher than 1000 Dalton was collected and lyophilized to dryness yielding 100 mg of the desired product as a light yellow solid.

Example 3-52

Synthesis of poly(4,4-trimethylene dipiperidine bispropanoic acid-co-5-(1,2-diol)-1,5,9-triazanonane-co-1,3-diamino propane)

The reaction mixture containing 0.125 g 4,4'-trimethylene dipiperidine bispropanoic acetate (Example 3-1), 0.05 g of 5-(1,2-diol)-1,5,9-triazanonane (Example 3-51(a)), and 0.3 g of 1,3-diamino propane was stirred at 100° C. for 18 hours. The resulting reaction mixture was dissolved in 5 mL of methanol poured into 50 mL of ethyl acetate. After filtering off the solvent, the residue was dissolved in 20 mL of DI water. The pH of the solution was adjusted to 2 by adding dilute HCl and the solution subjected to centrifugation using with Microsep membrane filter with a molecular weight cut off of 1000 Dalton. The fraction with molecular weight higher than 1000 Dalton was collected and lyophilized to dryness yielding 90 mg of the desired product as a light yellow solid.

Example 3-53

Synthesis of glycidol modified poly(4,4'-trimethylene dipiperidine bispropanoic acid-co-1,3-diamino propane)

To 0.26 g poly(4,4'-trimethylene dipiperidine bispropanoic acid-co-1,3-diamino propane) (Example 3-6) dissolved in 2 mL of ethanol was added 16.5 mg of glycidol. The reaction mixture at 140° C. for 30 minutes using a microwave reactor. The resulting reaction mixture was poured into 50 mL of ethyl acetate. After filtration, the residue was washed with ethyl acetate (3×50 mL). Subsequently, it was dissolved in 10 mL of DI water and was subjected to centrifugation using with Microsep membrane filter with a molecular weight cut off of 1000 Dalton. The fraction with molecular weight higher than 1000 Dalton was collected and lyophilized to dryness yielding 126 mg of the desired product as a light yellow solid.

Example 3-54

Synthesis of Guanidine terminated poly(4,4'-trimethylene dipiperidine bispropanoic acid-co-1,3-diamino propane)

To 0.3 g of poly(4,4'-trimethylene dipiperidine bispropanoic acid-co-1,3-diamino propane) (Example 3-6) dissolved in 2 mL of methanol was added 0.1 g of 1H-pyrazole-1-carboxamidine and 0.11 g of N,N'-diisopropylethylamine. The reaction mixture was stirred at 60° C. for 8 hours. The resulting reaction mixture was poured into 50 mL of ethyl acetate. After filtration, the residue was washed with ethyl acetate (3×50 mL). The resulting solid was dissolved in 2 mL of DI water and was passed through a PD-10 Sephadex column. The desired fractions were collected, lyophilized to dryness yielding 0.19 g of the polymer as a light yellow solid.

Example 3-55

Synthesis of Polyethylene glycol (PEG-4) terminated poly(4,4'-trimethylene dipiperidine bispropanoic acid-co-1,3-diamino propane)

To 0.128 g of poly(4,4'-trimethylene dipiperidine bispropanoic acid-co-1,3-diamino propane) (Example 3-6) dissolved in 5 mL of methanol solution was added 0.2 mL of triethyl amine followed by 0.075 g of m-dPEG4-NHS ester. The reaction solution was stirred at room temperature for 22 hours. The resulting reaction mixture was poured into 50 mL of ethyl acetate. After filtration, the residue was washed with ethyl acetate (5×50 mL). The residue was subsequently dissolved in 2 mL of DI water and the pH of the resulting solution was adjusted to 2 using dilute HCl was subjected to centrifugation using a Microsep membrane filter with a molecular weight cut off of 1000 Dalton. The fraction with molecular weight higher than 1000 Dalton was collected and lyophilized to dryness yielding 50 mg of the desired product as a light yellow solid.

Example 356

Synthesis of Polyethylene glycol (PEG-12) terminated poly(4,4'-trimethylene dipiperidine bispropanoic acid-co-1,3-diamino propane)

To 0.1 g of poly(4,4'-trimethylene dipiperidine bispropanoic acid-co-1,3-diamino propane) (Example 3-6) dissolved 5 mL of methanol was added 0.2 mL of triethyl amine followed by 0.12 g of m-dPEG12-NHS ester. The reaction solution was stirred at room temperature for 22 hours. The resulting reaction mixture was poured into 50 mL of ethyl acetate. After filtration, the residue was washed with ethyl acetate (5×50 mL). The residue was subsequently dissolved in 2 mL of DI water and the pH of the resulting solution was adjusted to 2 using dilute HCl. was subjected to centrifugation using with Microsep membrane filter with a molecular weight cut off of 1000 Dalton. The fraction with molecular weight higher than 1000 Dalton was collected and lyophilized to dryness yielding 60 mg of the desired product as a light yellow solid.

Example 3-57

Synthesis of monodispersed polymer (heptamer) of poly(4,4'-trimethylene dipiperidine bispropanoic acid-co-1,3-diamino propane)

Example 3-57(a)

Synthesis of 4,4'-trimethylene dipiperidine bispropanoic acid-1,3-diamino propane trimer The reaction mixture containing 3 g of 4,4'-trimethylene dipiperidine bispropanoic acetate (Example 3-2) and 4.1 g of mono N-boc-1,3-diamino propane was stirred at 100° C. for 18 hours. The resulting reaction mixture was purified by column chromatography using an amine modified silica column and the gradient solvent system ranging from 100% hexane to ethyl acetate/hexane (50/50)). The appropriate fraction was collected and removal of the solvent under reduced pressure produced 2.6 g of 4,4'-trimethylene dipiperidine bispropanoic acid-bis-BOC-1,3-diamino propane.

To 0.55 g of 4,4'-trimethylene dipiperidine bispropanoic acid-bis-boc-1,3-diamino propane dissolved in 5 mL of methanol was added 0.5 mL of concentrated HCl and the reaction mixture was stirred at 50° C. for 10 hours. After removal of the solvent under reduced pressure, the residue was dissolved in 10 mL of methanol/water (1:1) and was treated with 5 g of Amberlyst OH 26 resin. After stirring at room temperature for 3 hours, the resin was filtered off. The filtrate was evaporated dryness and the residue was lyophilized yielding 0.5 g of the product as a white solid.

Example 3-57(b)

Synthesis of 1-BOC-4,4'-trimethylene-1'-propanoic acid

To 2 g of 1-BOC-4,4'-trimethylene-1'propanoic methyl ester, 0.9 g of 50 wt % solution of aqueous sodium hydroxide was added and the reaction mixture was stirred at 60° C. for 15 hours. To this reaction mixture was added concentrated HCl until pH of the reaction reached 7.5. The reaction mixture was evaporated to dryness and residue was lyophilized to complete dryness. To this dry residue was added 10 mL of dichloromethane and the resulting mixture was stirred at room temperature for 30 minutes. After filtering off the insoluble particles, the filtrate was evaporated to dryness to give 0.7 g of a white solid product.

Example 3-57(c)

Synthesis of bis-boc-4,4'-trimethylene dipiperidine bispropanoic acid-1,3-diamino propane pentamer To 90 mg of 1-boc-4,4'-trimethylene-1'-propanoic acid (Example 3-57(b)) dissolved in 2 mL of dicloromethane/DMF (1:1 v/v) was added 38 mg of 1,1-carbonyl diimidazole. After stirring at room temperature for 1 hour, 0.05 g of 4,4'-trimethylene dipiperidine bispropanoic acid-1,3-diamino propane trimer (Example 3-57(a)) was added to reaction mixture. The resulting reaction mixture was stirred at room temperature for 20 hours. After removing the solvent under reduced pressure, the residue was purified by column chromatography using an amine modified silica column using a gradient solvent system ranging from 100% ethyl acetate to ethyl acetate/methanol (95/5)) yielding 80 mg of the product as a colorless oil. This oil was dissolved 2 mL of methanol followed by addition of 0.5 mL of concentrated HCl. The reaction mixture was stirred at 50° C. for 10 hours. The solvent was evaporated removed under reduced pressure and the residue was lyophilized to dry to yield 60 mg of the desired product as yellow viscous oil.

Example 3-57(d)

Synthesis of poly(4,4'-trimethylene dipiperidine bispropanoic acid-co-1,3-diamino propane) heptamer To 35 mg of 4,4'-trimethylene dipiperidine bispropanoic acid-1,3-diamino propane pentamer (Example 3-57(c)) dissolved in 1 mL of methanol was added 0.08 mL of triethyl amine and 24 mg of boc-(3-acrylamido) propyl amine. The reaction mixture was stirred at room temperature overnight. The reaction mixture was poured into 10 mL of ethyl acetate. The residue was isolated by filtration and was washed with ethyl acetate (3×10 mL). The residue was dried at room temperature under reduced pressure yielding 40 mg of a white solid. To this solid residue was added 2 mL of methanol and 0.5 mL of concentrated HCl. The resulting reaction mixture was added stirred at 50° C. for 10 hours. After removing the solvent under reduced pressure, residue was purified by preparative HPLC yielding 10 mg of the desired product as light yellow viscous oil.

The invention claimed is:

1. A compound comprising the structure of Formula (I):

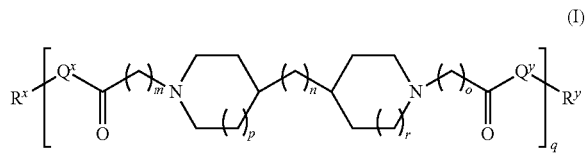

(I)

wherein:
i) m is 1, 2, or 3;
ii) n is 0, 1, 2, or 3;
iii) o is 1, 2, or 3;
iv) p is 0 or 1;
v) r is 0 or 1;
vi) q is an integer from 1 to 400;
vii) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
viii) $Q^y$ is NH—$R^w$, NH—$CH_2$—$R_w$, $(C_1-C_{10})$alkyl, or $(C_6-C_{14})$aryl, wherein $R^w$ is absent or a $(C_1-C_{10})$alkyl, $(C_2-C_9)$heteroalkyl, $(C_6-C_{14})$aryl, or $(C_2-C_9)$heteroaryl;
ix) $R^x$ and $R^y$ are each independently a pharmaceutically acceptable end group.
2. The compound according to claim 1 wherein n is 0.
3. The compound according to claim 1 wherein n is 1.
4. The compound according to claim 1 wherein n is 2.
5. The compound according to claim 1 wherein n is 3.
6. The compound according to claim 1 wherein p is 0.
7. The compound according to claim 1 wherein p is 1.
8. The compound according to claim 1 wherein r is 0.

9. The compound according to claim 1 wherein r is 1.

10. The compound according to claim 1 wherein p is 0 and r is 0.

11. The compound according to claim 1 wherein p is 1 and r is 1.

12. The compound according to claim 1 wherein n is 3; p is 1; and r is 1.

13. The compound according to claim 1 wherein n is 0; p is 1; and r is 1.

14. The compound according to claim 1 wherein n is 0; p is 0; and r is 0.

15. The compound according to claim 11 wherein:
i) $Q^x$ is —NH; and
ii) $Q^y$ is NH—$R^w$—, wherein $R^w$ is a $(C_1-C_{10})$alkyl, $(C_2-C_9)$heteroalkyl, $(C_6-C_{14})$aryl, or $(C_2-C_9)$heteroaryl.

16. The compound according to claim 12 wherein:
i) m is 2;
ii) o is 2;
iii) $Q^x$ is NH; and
iv) $Q^y$ is NH—$R^w$—, wherein $R^w$ is a $(C_3)$alkyl.

17. The compound according to claim 14 wherein:
i) $Q^x$ is NH; and
ii) $Q^y$ is N—$R^w$, wherein $R^w$ is absent or a $(C_1-C_{10})$alkyl, $(C_2-C_9)$heteroalkyl, $(C_6-C_{14})$aryl, or $(C_2-C_9)$heteroaryl.

18. The compound according to claim 12 wherein:
i) m is 2;
ii) o is 2;
iii) $Q^x$ is NH;
iv) $Q^y$ is NH—$R_w$—, wherein $R_w$ is a $(C_3)$alkyl
v) $R^x$ is a guanidinium chloride group represented by Formula (B),

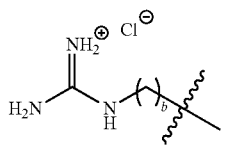

(B)

wherein b is 3; and
vi) $R^y$ is a guanidinium chloride group represented by Formula (B),

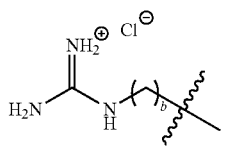

(B)

wherein b is 0.

19. The compound according to claim 1, wherein $R^x$ and $R^y$ are each independently H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, —O(O)C—$(C_1-C_{10})$alkyl, $(C_1-C_{10})$alkyl-COOH, $(C_3-C_{10})$cycloalkyl-COOH, —(O)CH$_3$, —OH, amide, a guanidino group represented by Formula (A)

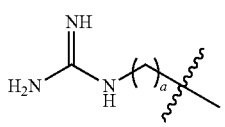

(A)

wherein a is an integer from 0 to 25,
a guanidinium chloride group represented by Formula (B),

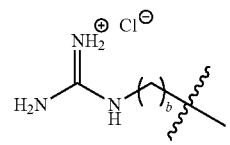

(B)

wherein b is an integer from 0 to 25,
a guanidinobenzene group represented by Formula (C),

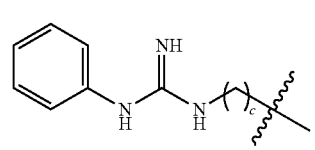

(C)

wherein c is an integer from 0 to 25,
a dihydroxy group, represented by Formula (D),

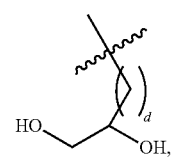

(D)

wherein d is an integer from 0 to 25, or
a polyethylene glycol group, represented by Formula (E)

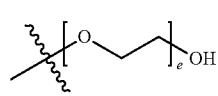

(E)

wherein e is an integer from 1 to 400.

20. The compound according to claim 19, wherein $R^x$ and $R^y$ are each independently selected from —(O)CH$_3$, a guanidino group represented by Formula (A)

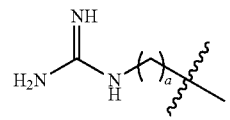

(A)

wherein a is an integer from 0 to 25, or
a guanidinobenzene group represented by Formula (C),

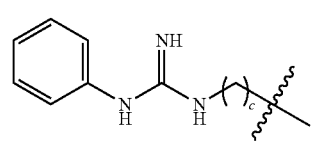

(C)

wherein c is an integer from 0 to 25.

21. A pharmaceutical composition comprising a compound according to claim 1.

22. The pharmaceutical composition according to claim 21 for use in the treatment of oral mucositis.

* * * * *